US012727790B2

(12) United States Patent
Lu et al.

(10) Patent No.: US 12,727,790 B2
(45) Date of Patent: Sep. 8, 2026

(54) BLOOD GLUCOSE DETECTION MODEL TRAINING METHOD, BLOOD GLUCOSE DETECTION METHOD AND SYSTEM, AND ELECTRONIC DEVICE

(71) Applicant: Huawei Technologies Co., Ltd., Shenzhen (CN)

(72) Inventors: Dong Lu, Shenzhen (CN); Luping Li, Beijing (CN); Maolin Chen, Beijing (CN)

(73) Assignee: Huawei Technologies Co., Ltd., Shenzhen (CN)

( * ) Notice: Subject to any disclaimer, the term of this patent is extended or adjusted under 35 U.S.C. 154(b) by 663 days.

(21) Appl. No.: 18/043,332

(22) PCT Filed: Aug. 16, 2021

(86) PCT No.: PCT/CN2021/112800

§ 371 (c)(1), (2) Date: Feb. 27, 2023

(87) PCT Pub. No.: WO2022/042356

PCT Pub. Date: Mar. 3, 2022

(65) Prior Publication Data

US 2023/0337946 A1 Oct. 26, 2023

(30) Foreign Application Priority Data

Aug. 31, 2020 (CN) ........................ 202010897327.9

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/1455* (2013.01); *A61B 5/681* (2013.01);
(Continued)

(58) Field of Classification Search
CPC . A61B 5/14532; A61B 5/1455; A61B 5/7275; A61B 5/1495; A61B 5/742;
(Continued)

(56) References Cited

U.S. PATENT DOCUMENTS 10,123,749 B2 11/2018 Kamimura
10,772,569 B2 9/2020 Jayaraman et al.
(Continued)

FOREIGN PATENT DOCUMENTS

CN 104008265 A * 8/2014
CN 104838415 A 8/2015
(Continued)

OTHER PUBLICATIONS

Enric Monte-Moreno: "Non-invasive estimate of blood glucose and blood pressure from a photoplethysmograph by means of machine learning techniques", Artificial Intelligence in Medicine, vol. 53, No. 2, Oct. 2011, total 12 pages.

*Primary Examiner* — Eric F Winakur
*Assistant Examiner* — Sienna C Pyle
(74) *Attorney, Agent, or Firm* — Slater Matsil, LLP

(57) ABSTRACT

In an embodiment a method for blood glucose detection includes obtaining, by a first electronic device, to-be-measured PPG (Photoplethysmography) data when the first electronic device detects a blood glucose detection instruction of a first user, performing feature extraction on the to-be-measured PPG data in order to obtain to-be-measured PPG feature data, inputting the to-be-measured PPG feature data into a pre-trained blood glucose detection model in order to obtain a blood glucose detection result and displaying first information according to the blood glucose detection result.

18 Claims, 16 Drawing Sheets

(51) Int. Cl.

| | |
|---|---|
| ***A61B 5/1455*** | (2006.01) |
| ***G16H 10/60*** | (2018.01) |
| ***G16H 50/70*** | (2018.01) |

(52) U.S. Cl.
CPC ........... *A61B 5/7275* (2013.01); *G16H 10/60* (2018.01); *G16H 50/70* (2018.01)

(58) Field of Classification Search
CPC ...... A61B 5/7267; A61B 5/746; G16H 10/60; G16H 50/70; G16H 40/63; G16H 50/30; G06N 20/00
See application file for complete search history.

(56) References Cited

U.S. PATENT DOCUMENTS

| | | | | |
|---|---|---|---|---|
| 2010/0265073 | A1 | 10/2010 | Harper | |
| 2011/0071464 | A1 | 3/2011 | Palerm | |
| 2014/0278220 | A1* | 9/2014 | Yuen | A61B 5/681 702/150 |
| 2019/0076031 | A1* | 3/2019 | Valys | A61B 5/02405 |
| 2019/0192086 | A1 | 6/2019 | Menon et al. | |
| 2019/0385721 | A1* | 12/2019 | Bowland | G16H 15/00 |
| 2020/0155081 | A1 | 5/2020 | Seo et al. | |
| 2020/0268265 | A1 | 8/2020 | Walsh et al. | |
| 2021/0321942 | A1* | 10/2021 | Pushpala | A61B 5/02416 |
| 2021/0358619 | A1* | 11/2021 | Vu | G16H 20/10 |
| 2022/0338764 | A1 | 10/2022 | Gao et al. | |

FOREIGN PATENT DOCUMENTS

| | | | |
|---|---|---|---|
| CN | 107028603 | A | 8/2017 |
| CN | 107374646 | A | 11/2017 |
| CN | 110141249 | A | 8/2019 |
| CN | 110243603 | A | 9/2019 |
| CN | 110623678 | A | 12/2019 |
| CN | 111345826 | A | 6/2020 |
| CN | 111588384 | A | 8/2020 |
| CN | 111599470 | A | 8/2020 |
| KR | 101724282 | B1 | 4/2017 |

* cited by examiner

BLOOD GLUCOSE DETECTION MODEL TRAINING METHOD, BLOOD GLUCOSE DETECTION METHOD AND SYSTEM, AND ELECTRONIC DEVICE

This application is a National Stage of International Patent Application No. PCT/CN2021/112800, filed on Aug. 16, 2021, which claims priority to Chinese Patent Application No. 202010897327.9, filed on Aug. 31, 2020, both of which are hereby incorporated by reference in their entireties.

TECHNICAL FIELD

This application relates to the field of blood glucose detection technologies, and in particular, to a blood glucose detection model training method, a blood glucose detection method and system, and an electronic device.

BACKGROUND

Diabetes is a group of metabolic diseases characterized by high blood glucose (venous plasma glucose, briefly referred to as blood glucose). The high blood glucose is caused by defective insulin secretion or an impaired biological action of insulin, or both defective insulin secretion and an impaired biological action of insulin. Diabetes need to be diagnosed through blood glucose detection, and blood glucose detection is performed in a timely manner to screen for diabetes, so that diabetes can be discovered and treated in a timely manner. High blood glucose in a long term can lead to many complications, such as chronic damage and dysfunction of various tissues, especially eyes, kidneys, a heart, blood vessels, and nerves, and life-threatening. Currently, there is no effective method to treat diabetes. Therefore, it is necessary for a diabetic to periodically detect blood glucose and monitor blood glucose in a timely manner.

Hypoglycemia is a group of syndromes that are caused by a variety of etiology and that are characterized by low blood glucose concentration and sympathetic nerve excitation and hypoxia in brain cells in clinical. Low blood glucose can stimulate a cardiovascular system, and lead to arrhythmia, myocardial infarction, a stroke, a coma, and the like. Long-term repeated severe low blood glucose attacks can lead to irreversible damage to a central nervous system, resulting in character changes in patients, and eventually mental disorder, dementia, and the like. Therefore, usually, it is necessary to pay attention to occurrence of the low blood glucose. In addition, the low blood glucose can also bring harm to a diabetic. Therefore, the diabetic also needs to pay attention to prevention of the low blood glucose.

It is important to provide a more convenient and accurate non-invasive blood glucose detection method to implement blood glucose detection, so as to further implement non-invasive screening for diabetes and non-invasive monitoring for blood glucose of a diabetic, and non-invasive screening and non-invasive monitoring for low blood glucose.

SUMMARY

This application provides a blood glucose detection model training method, a blood glucose detection method and system, and an electronic device, to implement more convenient and accurate non-invasive blood glucose detection, so that a user can perform blood glucose detection more conveniently, and can better perform blood glucose monitoring.

To resolve the foregoing technical problem, according to a first aspect, an implementation of this application provides a blood glucose detection model training method. The blood glucose detection model training method may be applied to a first electronic device. A process in which the first electronic device performs model training to generate a blood glucose detection model includes: The first electronic device obtains initial PPG data, where the initial PPG data includes PPG data of a group of healthy people and PPG data of a group of people with abnormal blood glucose. The first electronic device obtains, from each of the PPG data of the group of healthy people and the PPG data of the group of people with abnormal blood glucose, PPG data used to represent different blood glucose levels and uses the PPG data as difference adjustment data, and obtains difference adjustment values based on the difference adjustment data. The first electronic device performs, based on the difference adjustment values, difference amplification processing on the initial PPG data on which feature extraction is performed, to obtain model training PPG feature data, and performs model training based on the model training PPG feature data, to obtain the blood glucose detection model, where the initial PPG data on which feature extraction is performed is initial PPG feature data.

The first electronic device obtains, from each of the PPG data of the group of healthy people and the PPG data of the group of people with abnormal blood glucose, the PPG data used to represent the different blood glucose levels (a high blood glucose level and a low blood glucose level) and uses the PPG data as the difference adjustment data; obtains the difference adjustment values based on the difference adjustment data; performs difference amplification processing on the initial PPG feature data based on the difference adjustment values, to obtain the model training PPG feature data; and obtains the blood glucose detection model based on the model training PPG feature data. Compared with a manner in which feature extraction is directly performed on initial PPG data and model training is performed to generate a blood glucose detection model, a manner in which blood glucose information in the PPG data can be amplified differently by using the difference adjustment data resolves problems that the blood glucose information in the PPG data is weak and extraction of blood glucose-related features is difficult. Therefore, according to the PPG-based blood glucose detection model training method provided in this application, the blood glucose detection result output by the obtained blood glucose detection model can be more accurate. That is, when abnormal blood glucose screening is performed, a screening result can be more accurate.

In a possible implementation of the first aspect, the performing, based on the difference adjustment values, difference amplification processing on the initial PPG data on which feature extraction is performed, to obtain model training PPG feature data includes: obtaining differences between the initial PPG data on which feature extraction is performed and the difference adjustment values, and obtaining the model training PPG feature data based on the differences. That is, the differences between the initial PPG feature data and the difference adjustment values may be used as the model training PPG feature data.

In a possible implementation of the first aspect, the performing, based on the difference adjustment values, difference amplification processing on the initial PPG data on which feature extraction is performed, to obtain model training PPG feature data includes: obtaining sums of the initial PPG data on which feature extraction is performed and the difference adjustment values, and obtaining the model training PPG feature data based on the sums of the initial PPG data and the difference adjustment values. That is, the sums of the initial PPG feature data and the difference adjustment values may alternatively be used as the model training PPG feature data.

In a possible implementation of the first aspect, adjustment coefficients may be further set for the difference adjustment values, and differences (which may also be sums, products, quotients, or the like) between the initial PPG data on which feature extraction is performed and the difference adjustment values for which the adjustment coefficients are set are obtained and the differences are used as the model training PPG feature data.

Compared with a manner in which feature extraction is directly performed on initial PPG data and model training is performed to generate a blood glucose detection model, a manner in which blood glucose information in the PPG data can be amplified differently by using the difference adjustment data, and difference amplification processing is performed on the initial PPG feature data based on the difference adjustment values to obtain the model training PPG feature data resolves problems that the blood glucose information in the PPG data is weak and extraction of blood glucose-related features is difficult.

In a possible implementation of the first aspect, the obtaining, from each of the PPG data of the group of healthy people and the PPG data of the group of people with abnormal blood glucose, PPG data used to represent different blood glucose levels and using the PPG data as difference adjustment data includes: obtaining PPG data within a first time period from the PPG data of the group of healthy people and using the PPG data as first PPG data, and obtaining PPG data within a second time period from the PPG data of the group of healthy people and using the PPG data as second PPG data; obtaining PPG data within the first time period from the PPG data of the group of people with abnormal blood glucose and using the PPG data as third PPG data, and obtaining PPG data within the second time period from the PPG data of the group of people with abnormal blood glucose and using the PPG data as fourth PPG data; and obtaining the difference adjustment data based on the first PPG data, the second PPG data, the third PPG data, and the fourth PPG data.

In a possible implementation of the first aspect, a blood glucose level represented by the PPG data within the first time period is lower than a blood glucose level represented by the PPG data within the second time period. For example, the first time period may be a time period at night, and the second time period may be a time period in the daytime.

The first electronic device uses, as the difference adjustment data, the first PPG data and the second PPG data in the two different time periods that are obtained from the PPG data of the group of healthy people and that are used to represent different blood glucose levels and the third PPG data and the fourth PPG data in the two different time periods that are obtained from the PPG data of the group of people with abnormal blood glucose and that are used to represent different blood glucose levels. The first electronic device can differently amplify blood glucose information in the PPG data by using the difference adjustment data, so that problems that blood glucose information in a single piece of PPG data is weak and extraction of blood glucose-related features is difficult are resolved.

In a possible implementation of the first aspect, the obtaining, from each of the PPG data of the group of healthy people and the PPG data of the group of people with abnormal blood glucose, PPG data used to represent different blood glucose levels and using the PPG data as difference adjustment data includes: obtaining PPG data within a first value range from the PPG data of the group of healthy people and using the PPG data as first PPG data, and obtaining PPG data within a second value range from the PPG data of the group of healthy people and using the PPG data as second PPG data; obtaining PPG data within a third value range from the PPG data of the group of people with abnormal blood glucose and using the PPG data as third PPG data, and obtaining PPG data within a fourth value range from the PPG data of the group of people with abnormal blood glucose and using the PPG data as fourth PPG data; and obtaining the difference adjustment data based on the first PPG data, the second PPG data, the third PPG data, and the fourth PPG data.

In a possible implementation of the first aspect, a blood glucose level represented by the PPG data within the first value range is lower than a blood glucose level represented by the PPG data within the second value range, and a blood glucose level represented by the PPG data within the third value range is lower than a blood glucose level represented by the PPG data within the fourth value range.

The first electronic device uses, as the difference adjustment data, the first PPG data and the second PPG data in the two segments that are obtained from the PPG data of the group of healthy people and that are used to represent different blood glucose levels and the third PPG data and the fourth PPG data in the two segments that are obtained from the PPG data of the group of people with abnormal blood glucose and that are used to represent different blood glucose levels. The first electronic device can differently amplify blood glucose information in the PPG data by using the difference adjustment data, so that problems that blood glucose information in a single piece of PPG data is weak and extraction of blood glucose-related features is difficult are resolved.

In a possible implementation of the first aspect, the first electronic device may separately obtain PPG data in a plurality of segments such as three segments or four segments that is used to represent different blood glucose levels and uses the PPG data as the difference adjustment data, to improve accuracy of a detection result output by the generated blood glucose detection model.

In a possible implementation of the first aspect, that the first electronic device obtains difference adjustment values based on the difference adjustment data includes: performing feature extraction on the first PPG data to obtain first PPG feature data, and obtaining an average value of the first PPG feature data and using the average value as a first difference adjustment value; performing feature extraction on the second PPG data to obtain second PPG feature data, and obtaining an average value of the second PPG feature data and using the average value as a second difference adjustment value; performing feature extraction on the third PPG data to obtain third PPG feature data, and obtaining an average value of the third PPG feature data and using the average value as a third difference adjustment value; and performing feature extraction on the fourth PPG data to obtain fourth PPG feature data, and obtaining an average value of the fourth PPG feature data and using the average value as a fourth difference adjustment value.

In a possible implementation of the first aspect, the performing, based on the difference adjustment values, difference amplification processing on the initial PPG data on which feature extraction is performed, to obtain model training PPG feature data includes: separately performing, based on the first difference adjustment value, the second difference adjustment value, the third difference adjustment value, and the fourth difference adjustment value, feature difference amplification processing on the initial PPG data on which feature extraction is performed, to obtain the model training PPG feature data.

Compared with a manner in which feature extraction is directly performed on initial PPG data and model training is performed to generate a blood glucose detection model, a manner in which blood glucose information in the PPG data can be amplified differently by using the difference adjustment data, and difference amplification processing is performed on the initial PPG feature data based on the difference adjustment values to obtain the model training PPG feature data resolves problems that the blood glucose information in the PPG data is weak and extraction of blood glucose-related features is difficult.

In a possible implementation of the first aspect, the method further includes: performing first data processing on PPG data; and performing feature extraction on the PPG data on which the first data processing is performed. This facilitates subsequent model training and data processing in blood glucose detection. The first data processing includes data extraction processing, to extract PPG signal information in the PPG data.

In a possible implementation of the first aspect, the method further includes: performing second data processing on PPG feature data, so that formats of the PPG feature data are more unified; and performing average value calculation on the PPG feature data on which the second data processing is performed, to facilitate subsequent model training and data processing in blood glucose detection, where the second data processing includes data consistency processing.

In a possible implementation of the first aspect, the method further includes: The first electronic device obtains the initial PPG data from a server that establishes a communication connection to the first electronic device and that stores the initial PPG data.

In a possible implementation of the first aspect, that the first electronic device obtains initial PPG data includes: The first electronic device obtains the initial PPG data based on a preset model training period. Alternatively, the first electronic device obtains the initial PPG data when detecting an operation of opening a blood glucose detection application by a user.

In a possible implementation of the first aspect, the model training period may be any time such as one week or one month.

In a possible implementation of the first aspect, the PPG data of the group of people with abnormal blood glucose is PPG data of a group of people with high blood glucose and/or PPG data of a group of people with low blood glucose.

If the PPG data of the group of people with abnormal blood glucose is the PPG data of the group of people with high blood glucose, the blood glucose detection model may be used to screen for diabetes and monitor blood glucose of a diabetic. The blood glucose detection model may also be referred to as a high blood glucose risk screening model.

If the PPG data of the group of people with abnormal blood glucose is the PPG data of the group of people with low blood glucose, the blood glucose detection model may be used to screen for hypoglycemia and monitor blood glucose of a person with hypoglycemia. The blood glucose detection model may also be referred to as a low blood glucose risk screening model.

If the PPG data of the group of people with abnormal blood glucose includes both the PPG data of the group of people with high blood glucose and the PPG data of the group of people with low blood glucose, the blood glucose detection model may be used to screen for diabetes and monitor blood glucose of a diabetic, and may also be used to screen for hypoglycemia and monitor blood glucose of a person with hypoglycemia.

In a possible implementation of the first aspect, the first electronic device may be a terminal device such as a mobile phone or a computer.

According to a second aspect, an implementation of this application further provides a blood glucose detection method. The method may be applied to a first electronic device. The method includes: The first electronic device obtains to-be-measured PPG data to be detected; and performs feature extraction on the to-be-measured PPG data to obtain to-be-measured PPG feature data, and inputs the to-be-measured PPG feature data into a pre-trained blood glucose detection model, to obtain a blood glucose detection result, where the blood glucose detection model is generated by performing model training based on model training PPG feature data, the model training PPG feature data is obtained by performing, based on difference adjustment values, difference amplification processing on initial PPG data on which feature extraction is performed, the initial PPG data includes PPG data of a group of healthy people and PPG data of a group of people with abnormal blood glucose, and the difference adjustment values are obtained based on difference adjustment data that is in the PPG data of the group of healthy people and the PPG data of the group of people with abnormal blood glucose and that is used to represent different blood glucose levels.

That is, a process of generating the blood glucose detection model is as follows: The first electronic device obtains, from each of the PPG data of the group of healthy people and the PPG data of the group of people with abnormal blood glucose, PPG data used to represent different blood glucose levels (a high blood glucose level and a low blood glucose level) and uses the PPG data as the difference adjustment data, and obtains the difference adjustment values based on the difference adjustment data. The first electronic device performs difference amplification processing on the initial PPG feature data based on the difference adjustment values, to obtain the model training PPG feature data, and obtains the blood glucose detection model based on the model training PPG feature data. Compared with a manner in which feature extraction is directly performed on initial PPG data and model training is performed to generate a blood glucose detection model, a manner in which blood glucose information in the PPG data can be amplified differently by using the difference adjustment data resolves problems that the blood glucose information in the PPG data is weak and extraction of blood glucose-related features is difficult. Therefore, according to the PPG-based blood glucose detection method provided in this application, the blood glucose detection result output by the blood glucose detection model can be more accurate. That is, when abnormal blood glucose screening is performed, a screening result can be more accurate.

In a possible implementation of the second aspect, that the first electronic device obtains to-be-measured PPG data includes: The first electronic device obtains the to-be-measured PPG data based on a preset detection period; or the first electronic device opens a blood glucose detection application, and displays an application interface, where a blood glucose detection control is displayed in the application interface; and the first electronic device obtains the to-be-measured PPG data when detecting a trigger operation performed by a user on the blood glucose detection control.

In a possible implementation of the second aspect, the detection period may be any time such as 12 hours, one day, or two days.

In a possible implementation of the second aspect, the blood glucose detection result includes a blood glucose abnormality risk probability value, and the method further includes: obtaining a blood glucose abnormality risk level based on the blood glucose abnormality risk probability value, where the blood glucose abnormality risk level includes a high risk; collecting statistics about a quantity of times that a risk level is a high risk within a preset time period; and if the quantity of high-risk times exceeds a security threshold, generating first notification information, and sending the first notification information to an associated device corresponding to an associated person; or if the quantity of high-risk times is less than a security threshold, generating second notification information, and sending the second notification information to an associated device corresponding to an associated person.

The associated person may learn of a blood glucose level of the user by using the first notification information and the second notification information. The associated person may be a relative or a friend of the user, or may be a doctor.

In a possible implementation of the second aspect, the blood glucose abnormality risk probability value is a high blood glucose risk probability value, and the blood glucose abnormality risk level is a high blood glucose risk level.

In a possible implementation of the second aspect, the blood glucose abnormality risk probability value is a low blood glucose risk probability value, and the blood glucose abnormality risk level is a low blood glucose risk level.

In a possible implementation of the second aspect, the security threshold may be 5. For example, if a quantity of times of continuously detecting a high risk in a month exceeds 5, it is considered that the quantity exceeds the security threshold. Alternatively, if a total quantity of high-risk times in a month exceeds 5, it is considered that the quantity exceeds the security threshold.

In a possible implementation of the second aspect, the blood glucose detection application further includes an associated person setting control, and the method further includes: receiving a trigger operation performed by the user on the associated person setting control, and performing an associated person adding, modification, or deletion operation based on the trigger operation of the user.

In a possible implementation of the second aspect, the blood glucose detection application further includes a security threshold setting control, and the method further includes: receiving a security threshold setting performed by the user by using the security threshold setting control.

In a possible implementation of the second aspect, the method further includes: displaying blood glucose detection information in the application interface, where the blood glucose detection information includes blood glucose abnormality risk screening result information and user reminder information that are generated based on the blood glucose detection result, the blood glucose abnormality risk screening result information includes a blood glucose abnormality risk level, and the user reminder information includes a quantity of blood glucose detection times, a quantity of times that a quantity of high-risk times exceeds a security threshold, and suggestion information used for health intervention.

The blood glucose abnormality risk screening result information may enable the user to clearly know a current blood glucose abnormality risk level. In addition, the user may intervene in advance by using the user reminder information, so that the user pays attention to blood glucose screening, diet, exercise, and the like, to improve user experience.

In a possible implementation of the second aspect, the first electronic device obtains the to-be-measured PPG data from a wearable device that establishes a communication connection to the first electronic device and that is configured to detect PPG data.

In a possible implementation of the second aspect, the first electronic device may be a terminal device such as a mobile phone or a computer.

In a possible implementation of the second aspect, the blood glucose abnormality risk probability value may be a high blood glucose risk probability value or a low blood glucose risk probability value.

According to a third aspect, an implementation of this application provides a blood glucose detection model training system. The system includes a first electronic device and a server. The server is configured to send initial PPG data to the first electronic device, where the initial PPG data includes PPG data of a group of healthy people and PPG data of a group of people with abnormal blood glucose. The first electronic device is configured to: receive the initial PPG data; obtain, from each of the PPG data of the group of healthy people and the PPG data of the group of people with abnormal blood glucose, PPG data used to represent different blood glucose levels and use the PPG data as difference adjustment data, and obtain difference adjustment values based on the difference adjustment data; and perform, based on the difference adjustment values, difference amplification processing on the initial PPG data on which feature extraction is performed, to obtain model training PPG feature data, and perform model training based on the model training PPG feature data, to obtain a blood glucose detection model.

In a possible implementation of the third aspect, the first electronic device may be a terminal device such as a mobile phone or a computer.

The blood glucose detection model training system provided in this application includes the first electronic device configured to perform the blood glucose detection model training method according to any one of the first aspect and/or the possible implementations of the first aspect, and therefore can also implement beneficial effects (or advantages) of the blood glucose detection model training method according to the first aspect.

According to a fourth aspect, an implementation of this application provides a blood glucose detection system. The system includes a first electronic device and a second electronic device. The second electronic device is configured to send to-be-measured PPG data to be detected to the first electronic device. The first electronic device is configured to: receive the to-be-measured PPG data; and perform feature extraction on the to-be-measured PPG data to obtain to-be-measured PPG feature data, and input the to-be-measured PPG feature data into a pre-trained blood glucose detection model, to obtain a blood glucose detection result, where the blood glucose detection model is generated by performing model training based on model training PPG feature data, the model training PPG feature data is obtained by performing, based on difference adjustment values, difference amplification processing on initial PPG data on which feature extraction is performed, the initial PPG data includes PPG data of a group of healthy people and PPG data of a group of people with abnormal blood glucose, and the difference adjustment values are obtained based on difference adjustment data that is in the PPG data of the group of healthy people and the PPG data of the group of people with abnormal blood glucose and that is used to represent different blood glucose levels.

In a possible implementation of the fourth aspect, the second electronic device may be a wearable device such as a watch or a band.

The blood glucose detection system provided in this application includes the first electronic device configured to perform the blood glucose detection method according to any one of the second aspect and/or the possible implementations of the second aspect, and therefore can also implement beneficial effects (or advantages) of the blood glucose detection method according to the second aspect.

According to a fifth aspect, an implementation of this application provides an electronic device, including a memory, configured to store a computer program, where the computer program includes program instructions; and a control component, configured to execute the program instructions, so that the electronic device performs the blood glucose detection model training method according to any one of the first aspect and/or the possible implementations of the first aspect, or the electronic device performs the blood glucose detection method according to any one of the second aspect and/or the possible implementations of the second aspect.

According to a sixth aspect, an implementation of this application provides a computer-readable storage medium. The computer-readable storage medium stores a computer program, the computer program includes program instructions, and the program instructions are run by a computer, so that an electronic device performs the blood glucose detection model training method according to any one of the first aspect and/or the possible implementations of the first aspect, or the electronic device performs the blood glucose detection method according to any one of the second aspect and/or the possible implementations of the second aspect.

BRIEF DESCRIPTION OF THE DRAWINGS

To describe the technical solutions in this application more clearly, the following briefly describes the accompanying drawings used for describing the implementations.

DETAILED DESCRIPTION OF ILLUSTRATIVE EMBODIMENTS

The following further clearly and completely describes the technical solutions of this application with reference to the accompanying drawings.

Non-invasive diabetes screening and blood glucose detection technologies are more convenient for users and provide better user experience. As diabetics increase, it is important to provide a more convenient and accurate non-invasive blood glucose detection method to implement non-invasive screening for diabetes and non-invasive monitoring for blood glucose of a diabetic.

In the conventional technology, there are the following two non-invasive diabetes screening methods:

Method 1: Based on a diabetes screening questionnaire and basic personal data of a user, a diabetes screening result is provided through score statistics.

For example, the "Chinese version of diabetes risk assessment scale" provides entries such as an age, systolic pressure, body parameters, a waist circumference, a gender, a diabetes history, a family history, an exercise amount, and a diet. Each entry includes entry options and corresponding scores. The user fills in the "Chinese version of diabetes risk assessment scale" based on an actual situation of the user and selects a specific entry option in each entry. A score is calculated based on the user's selection, and a diabetes screening result of the user can be obtained based on the score.

This method has a coarse screening granularity. Some indicators (such as the exercise amount and the diet) are difficult to be quantitatively analyzed, which affects screening accuracy. Some indicators (such as the systolic pressure value) need to be measured by using professional instruments and are inconvenient to be used. In addition, a large amount of personal data easily generates noise, which also affects accuracy of the screening result.

Method 2: Based on medical data, a diabetes screening model is constructed by using a machine learning method, and a diabetes screening result is provided for a user.

For example, a diabetes screening model including indicator elements such as an age, a family history of type 2 diabetes mellitus (T2DM), a body mass index (Body Mass Index, BMI), high density lipoprotein cholesterol, low density lipoprotein cholesterol triglyceride, and C-reactive protein is provided. The indicator information corresponding to the user is input into the diabetes screening model, so that a diabetes screening result can be obtained.

This method depends on many and complex indicators. Some indicator information (such as the family history of T2DM) is difficult to be obtained, and some indicator information (such as cholesterol, triglyceride, and C-reactive protein) is even more difficult to be obtained than directly invasive detection of blood glucose. Therefore, it is inconvenient to screen for diabetes, and a requirement of the user for daily screening for diabetes cannot be met.

Figures 1, 2:
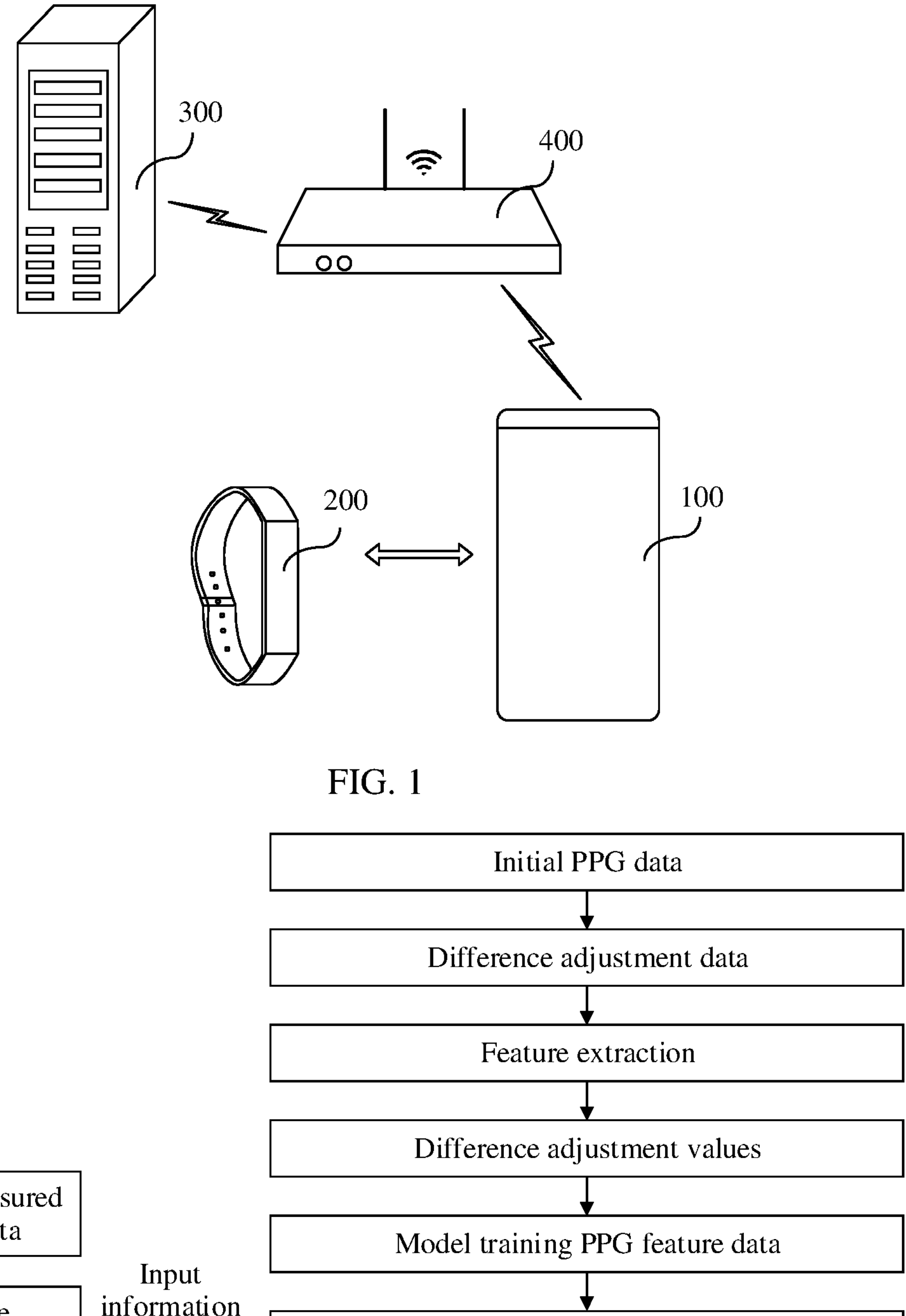
FIG. 1 shows a system to which a blood glucose detection model training method and a blood glucose detection method provided in this application are applied according to some implementations of this application.
FIG. 2 is a schematic diagram of a process of a blood glucose detection model training method and a blood glucose detection method according to some implementations of this application.

FIG. 1 shows a system. The system includes a mobile phone 100, a band 200, a server (which may also be referred to as a network server, a cloud server, or a cloud) 300, and an access point (Access Point, AP) router 400.

The mobile phone 100 establishes a communication connection to the AP router 400, to access a wireless local area network (Wireless Local Area Network, WLAN) (for example, wireless fidelity (Wireless Fidelity, Wi-Fi)) provided by the AP router 400. The mobile phone 100 may access the server 300 by using the AP router 400.

The mobile phone 100 may establish a communication connection to the band 200 through Bluetooth (Bluetooth), or the band 200 may establish a communication connection to the mobile phone 100 through a mobile hotspot (Mobile Hotspot) shared by the mobile phone 100. Certainly, the band 200 may also establish a communication connection to the mobile phone 100 by using another near field communications technology.

In addition, the band 200 may also establish a communication connection to the AP router 400, to access a wireless local area network provided by the AP router 400. In this case, the mobile phone 100 and the band 200 may establish a communication connection through the wireless local area network provided by the AP router 400.

This application provides a blood glucose detection model training method and a blood glucose detection method based on a photoplethysmography (Photoplethysmography, PPG) principle. The blood glucose detection model training method and the blood glucose detection method may be applied to the foregoing system. PPG is a non-invasive blood glucose detection technique for detecting a change of a blood volume in human tissues by using photoelectric means.

In this application, the server 300 may be a PPG data storage server in a hospital. The server 300 stores a large amount of PPG data (or may be referred to as PPG signal data). The PPG data includes PPG data of a group of healthy people and PPG data of a group of people with abnormal blood glucose. The PPG data stored in the server 300 is reported by a plurality of wearable devices (such as a band and a watch) having a PPG detection function to the server 300 for storage. Certainly, the server 300 may alternatively be a PPG data storage server corresponding to a PPG-based blood glucose detection application installed on a wearable device, and stores PPG data of a plurality of users.

The band 200 has a PPG detection function. The band 200 is worn on a wrist of a user, and performs PPG detection to obtain PPG data.

The mobile phone 100 may obtain a specific amount of PPG data from the server 300 and use the PPG data as initial PPG data, and perform model training based on the initial PPG data to obtain a blood glucose detection model used for blood glucose detection.

The mobile phone 100 may use the PPG data obtained by the band 200 through detection as to-be-measured PPG data, and input the to-be-measured PPG data into the blood glucose detection model to obtain a blood glucose detection result.

Refer to FIG. 2. In the blood glucose detection model training method provided in this application, a process in which the mobile phone 100 generates the blood glucose detection model includes: The mobile phone 100 obtains initial PPG data from the server 300, where the initial PPG data includes PPG data of a group of healthy people and PPG data of a group of people with abnormal blood glucose. The mobile phone 100 obtains, from each of the PPG data of the group of healthy people and the PPG data of the group of people with abnormal blood glucose, PPG data used to represent different blood glucose levels and uses the PPG data as difference adjustment data, and performs feature extraction on the difference adjustment data to obtain difference adjustment feature data. The mobile phone 100 obtains difference adjustment values based on the difference adjustment feature data, and then performs, based on the difference adjustment values, difference amplification processing on the initial PPG data on which feature extraction is performed, to obtain model training PPG feature data. The mobile phone 100 performs model training based on the model training PPG feature data, to obtain a blood glucose detection model. Blood glucose information in the PPG data can be amplified differently by using the difference adjustment data, so that a problem that the blood glucose information in the PPG data is weak is resolved. Therefore, according to the PPG-based blood glucose detection model training method provided in this application, the blood glucose detection result output by the obtained blood glucose detection model during blood glucose detection can be more accurate. That is, when abnormal blood glucose screening is performed, a screening result can be more accurate.

Still refer to FIG. 2. In the blood glucose detection method provided in this application, a process in which the mobile phone 100 obtains the blood glucose detection result includes: When the mobile phone 100 needs to perform blood glucose detection, the mobile phone 100 obtains PPG data from the band 200 and uses the PPG data as to-be-measured PPG data. The mobile phone 100 performs feature extraction on the to-be-measured PPG data, and then inputs the to-be-measured PPG data as input information into the pre-trained blood glucose detection model, so that a blood glucose detection result used as information output by the blood glucose detection model can be obtained, to implement convenient and accurate non-invasive blood glucose detection.

In this application, the group of healthy people may be a group of people that do not suffer from diabetes, that is, a group of people whose blood glucose level is a normal blood glucose level. In this case, the PPG data of the group of healthy people is PPG data corresponding to the normal blood glucose level.

The group of people with abnormal blood glucose may be a group of people that suffer from diabetes, that is, a group of people whose blood glucose level is a high blood glucose level. In this case, the PPG data of the group of people with abnormal blood glucose may be high blood glucose PPG data corresponding to the high blood glucose level.

The group of people with abnormal blood glucose may also be a group of people that suffer from hypoglycemia, that is, a group of people whose blood glucose level is a low blood glucose level. In this case, the PPG data of the group of people with abnormal blood glucose may be low blood glucose PPG data corresponding to the low blood glucose level.

A process in which the mobile phone 100 generates the blood glucose detection model and a process in which the mobile phone 100 obtains the blood glucose detection result are described in detail below.

Figure 3A:
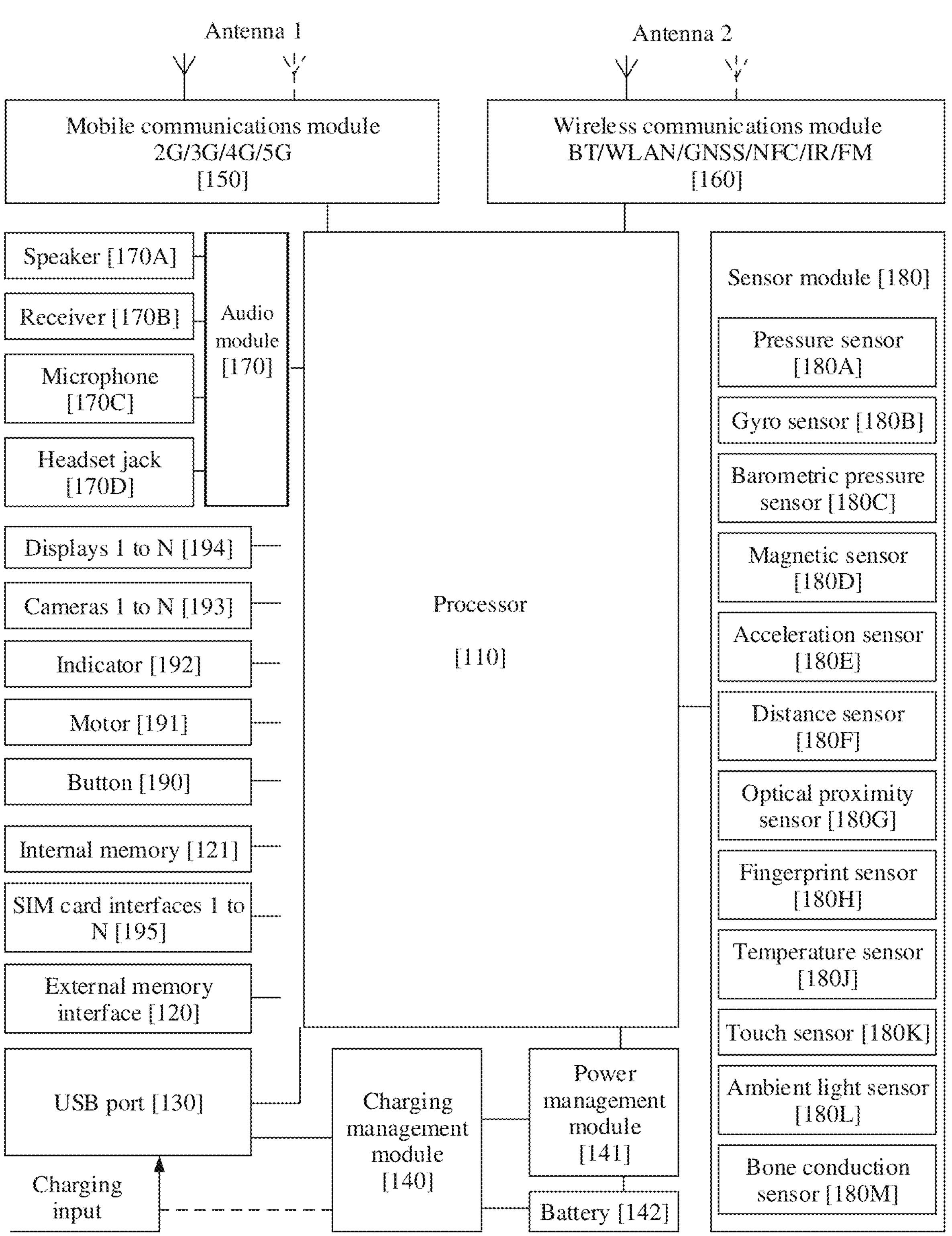
FIG. 3A is a schematic diagram of a structure of a mobile phone 100 according to some implementations of this application.

FIG. 3A is a schematic diagram of a structure of an example mobile phone 100 according to an embodiment of this application.

The mobile phone 100 may include a processor 110, an external memory interface 120, an internal memory 121, a USB port 130, a charging management module 140, a power management module 141, a battery 142, an antenna 1, an antenna 2, a mobile communications module 150, a wireless communications module 160, an audio module 170, a speaker 170A, a receiver 170B, a microphone 170C, a headset jack 170D, a sensor module 180, a button 190, a motor 191, an indicator 192, a camera 193, a display 194, a SIM card interface 195, and the like. The sensor module 180 may include a pressure sensor 180A, a gyro sensor 180B, a barometric pressure sensor 180C, a magnetic sensor 180D, an acceleration sensor 180E, a distance sensor 180F, an optical proximity sensor 180G, a fingerprint sensor 180H, a temperature sensor 180J, a touch sensor 180K, an ambient light sensor 180L, a bone conduction sensor 180M, and the like.

It may be understood that the structure shown in this embodiment of this application does not constitute a limitation on the mobile phone 100. In some other embodiments of this application, the mobile phone 100 may include more or fewer components than those shown in the figure, or combine some components, or split some components, or have different component arrangements.

The processor 110 may include one or more processing units. For example, the processor 110 may include an application processor (Application Processor, AP), a modem processor, a graphics processing unit (Graphics Processing Unit, GPU), an image signal processor (Image Signal Processor, ISP), a controller, a video codec, a digital signal processor (Digital Signal Processor, DSP), a baseband processor, and/or a neural-network processing unit (Neural-network Processing Unit, NPU). Different processing units may be independent components, or may be integrated into one or more processors.

The processor 110 may generate an operation control signal based on an instruction operation code and a time sequence signal, to complete control of instruction reading and instruction execution.

A memory may be further disposed in the processor 110, and is configured to store instructions and data. In some embodiments, the memory in the processor 110 is a cache. The memory may store instructions or data that has been used or is cyclically used by the processor 110. If the processor 110 needs to use the instructions or the data again, the processor may directly invoke the instructions or the data from the memory. This avoids repeated access and reduces a waiting time of the processor 110, to improve system efficiency.

In some embodiments, the processor 110 may include one or more interfaces. The interface may include an inter-integrated circuit (Inter-integrated Circuit, I2C) interface, an inter-integrated circuit sound (Inter-integrated Circuit Sound, I2S) interface, a pulse code modulation (Pulse Code Modulation, PCM) interface, a universal asynchronous receiver/transmitter (Universal Asynchronous Receiver/Transmitter, UART) interface, a mobile industry processor interface (Mobile Industry Processor Interface, MIPI), a general-purpose input/output (General-Purpose Input/output, GPIO) interface, a subscriber identity module (Subscriber Identity Module, SIM) interface, and the like.

The USB connector 130 is a connector that conforms to a USB standard specification, may be configured to connect the mobile phone 100 to a peripheral device, and may be specifically a standard USB connector (for example, a Type-C connector), a mini USB connector, a micro USB connector, or the like. The USB connector 130 may be configured to connect to a charger to charge the mobile phone 100, or may be configured to transmit data between the mobile phone 100 and a peripheral device. Alternatively, the connector may be configured to connect to another electronic device, for example, an AR device. The USB connector 130 may also be used to implement the foregoing USB transmission channel. In some implementation solutions, the processor 110 may support a USB, and a USB standard specification may be USB1.x, USB2.0, USB3.x, or USB4.

A wireless communication function of the mobile phone 100 may be implemented through the antenna 1, the antenna 2, the mobile communications module 150, the wireless communications module 160, the modem processor, the baseband processor, and the like.

The mobile communications module 150 may provide a wireless communication function that includes 2G/3G/4G/5G or the like and that is applied to the mobile phone 100. The mobile phone 100 may access the server 300 by using the mobile communications module 150.

The wireless communications module 160 may provide a wireless communication solution that includes a WLAN (for example, Wi-Fi), Bluetooth, a global navigation satellite system (Global Navigation Satellite System, GNSS), frequency modulation (Frequency Modulation, FM), a near field communication (Near Field Communication, NFC) technology, an infrared (Infrared, IR) technology, or the like and that is applied to the mobile phone 100. The wireless communications module 160 may be one or more components integrating at least one communications processor module. The wireless communications module 160 receives an electromagnetic wave through the antenna 2, performs frequency modulation and filtering processing on an electromagnetic wave signal, and sends a processed signal to the processor 110. The wireless communications module 160 may further receive a to-be-sent signal from the processor 110, perform frequency modulation and amplification on the signal, and convert the signal into an electromagnetic wave for radiation through the antenna 2.

The wireless communications module 160 may include a module configured to implement local area network transmission, for example, a Wi-Fi communications module or a Bluetooth communications module (or the wireless communications module 160 may include a component configured to implement local area network transmission, for example, a Wi-Fi chip or a Bluetooth chip), and is configured to implement the foregoing communication connection to the AP router 400.

In some embodiments, in the mobile phone 100, the antenna 1 and the mobile communications module 150 are coupled, and the antenna 2 and the wireless communications module 160 are coupled, so that the mobile phone 100 can communicate with a network and another device by using a wireless communications technology.

The internal memory 121 may be configured to store computer-executable program code. The executable program code includes instructions. The internal memory 121 may include a program storage area and a data storage area. The program storage area may store an operating system, an application required by at least one function (for example, a sound playing function or an image playing function), and the like. The data storage area may store data (such as audio data and an address book) and the like created during use of the mobile phone 100. In addition, the internal memory 121 may include a high-speed random access memory, or may include a nonvolatile memory, for example, at least one magnetic disk storage device, a flash memory, or a universal flash storage (universal flash storage, UFS). The processor 110 performs various function applications of the mobile phone 100 and data processing by running the instructions stored in the internal memory 121 and/or instructions stored in the memory disposed in the processor, for example, performs the blood glucose detection model training method and the blood glucose detection method provided in this application.

Figure 3B:
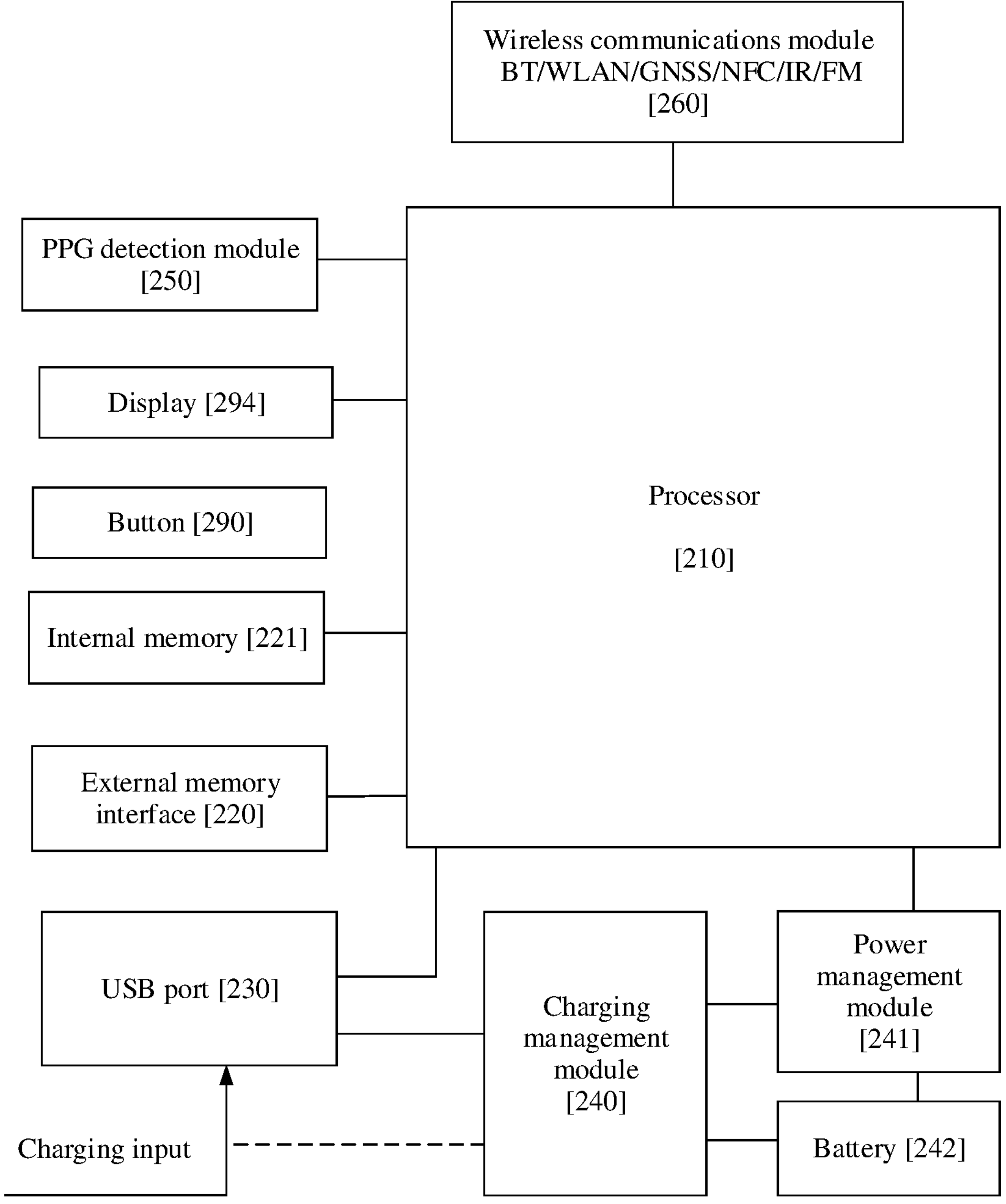
FIG. 3B is a schematic diagram of a structure of a band 200 according to some implementations of this application.

FIG. 3B is a schematic diagram of a structure of an example band 200 according to an embodiment of this application.

The band 200 may include a processor 210, an external memory interface 220, an internal memory 221, a USB port 230, a charging management module 240, a power management module 241, a battery 242, a PPG detection module 250, a wireless communications module 260, a button 290, a display 294, and the like.

It may be understood that the structure shown in this embodiment of this application does not constitute a limitation on the band 200. In some other embodiments of this application, the band 200 may include more or fewer components than those shown in the figure, or combine some components, or split some components, or have different component arrangements.

The PPG detection module 250 includes a light source (for example, a photoelectric emitter) and a photodetector (for example, a photoelectric receiver). The light source is configured to emit detection light used to irradiate a human body tissue, and the photodetector is configured to receive detection light that passes through a human body tissue. The PPG detection module 250 uses the detection light to pass through the human body tissue. Some of light emitted by the light source is absorbed by the human body tissue, and the other is received by the photodetector, so that PPG data can be collected. The PPG data reflects a change of a blood volume, so that blood glucose can be detected based on the PPG data.

The detection light emitted by the light source may be red light, infrared light, green light, or light of another type.

In addition, the PPG detection module 250 may include only one pair of light sources and photodetectors for PPG detection, so that PPG data can be collected on a single channel. Alternatively, the PPG detection module 250 may include more than two pairs of light sources and photodetectors for PPG detection, so that PPG data can be collected on a multi-channel. Quantities of light sources and photodetectors may be set based on a requirement.

After obtaining the PPG data, the band 200 may store the PPG data locally on the band 200, or may send the PPG data to the mobile phone 100 for storage.

In this application, a specific structure of the PPG detection module 250 is not described in detail. A common PPG detection module in the conventional technology may be selected for the PPG detection module 250, or another structure may be selected.

The wireless communications module 260 may provide a wireless communication solution that includes a WLAN (for example, Wi-Fi), Bluetooth, or the like and that is applied to the band 200. The wireless communications module 260 may be one or more components integrating at least one communications processor module. The wireless communications module 260 may include a component configured to implement local area network transmission, for example, a Wi-Fi chip or a Bluetooth chip, and is configured to implement the foregoing communication connection to the mobile phone 100 or the AP router 10.

In addition, functions of other components in the band 200 are the same as or similar to those of corresponding components in the mobile phone 100. Details are not described herein again.

In this application, an example in which a wearable device is the band 200 is used for description, but the wearable device may alternatively be another wearable device such as a watch.

Figure 4A:
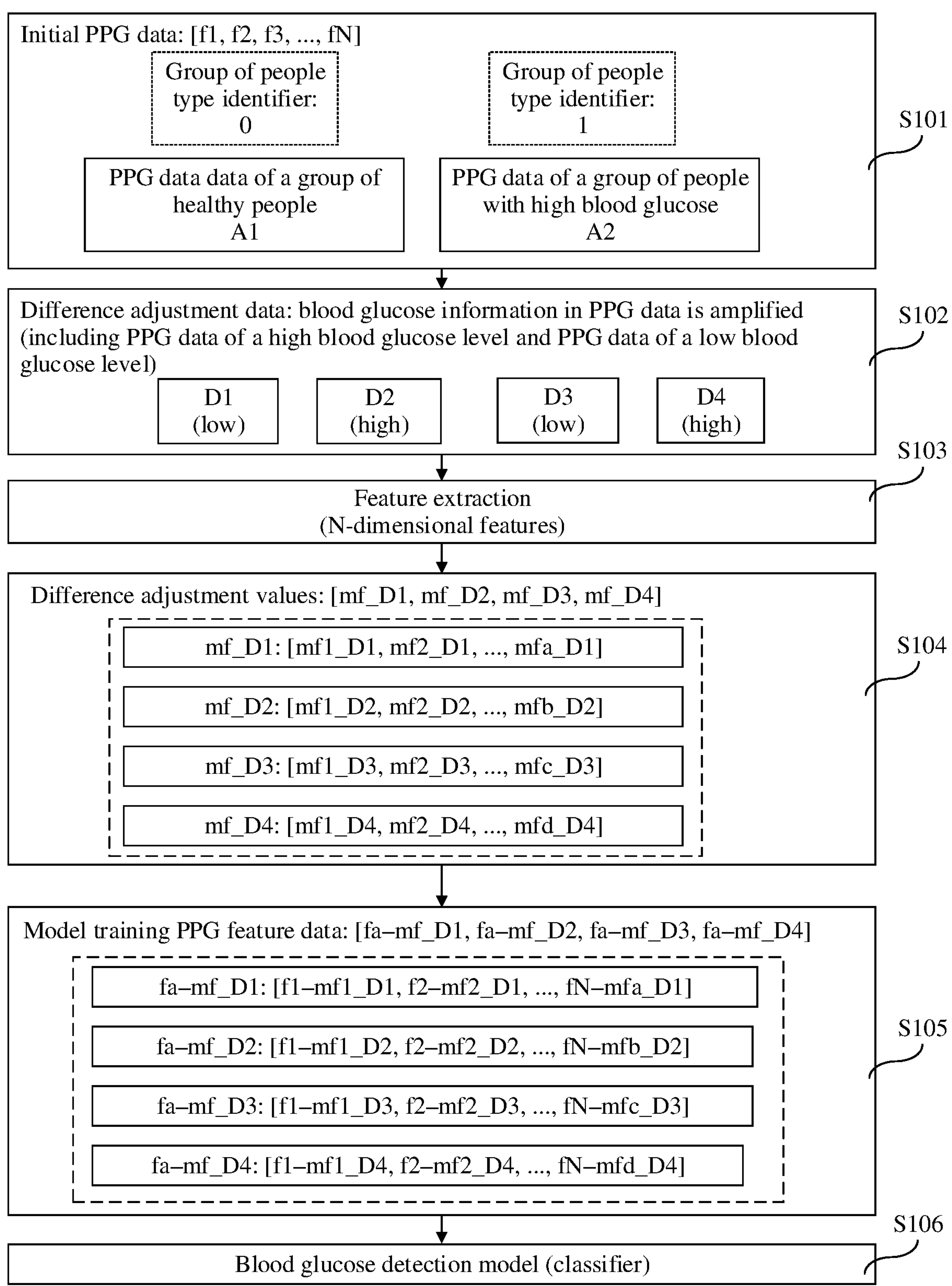
FIG. 4A is a schematic flowchart of a blood glucose detection model training method according to some implementations of this application.

Refer to FIG. 4A. In an implementation of a blood glucose detection model training method provided in this application, PPG data of a group of people with abnormal blood glucose is PPG data of a group of people with high blood glucose. In this case, a process in which the mobile phone 100 generates a blood glucose detection model includes the following steps.

S101: The mobile phone 100 obtains initial PPG data from the server 300.

The mobile phone 100 may include a blood glucose detection application. When the mobile phone 100 detects an operation of opening the blood glucose detection application by the user for the first time, the mobile phone 100 sends an initial PPG data obtaining request to the server 300.

The server 300 receives the initial PPG data obtaining request, selects, based on the initial PPG data obtaining request and according to a preset PPG data selection rule, some PPG data from a plurality of pieces of PPG data stored in the server 300 as initial PPG data (where the initial PPG data is a data set), and sends the initial PPG data to the mobile phone 100. The PPG data selection rule may include a time period selection rule (for example, selection is performed from stored PPG data in a recent month), a quantity selection rule (for example, N pieces are selected, where N may be 100), a group of people type selection rule (for example, a group of healthy people and a group of people with high blood glucose are included), or the like.

The initial PPG data determined by the server 300 includes N pieces of PPG data: f1, f2, f3, . . . , and fN, where N is a positive integer greater than 2. In addition, the initial PPG data includes PPG data A1 of a group of healthy people and PPG data A2 of a group of people with high blood glucose. An amount of PPG data A1 of the group of healthy people is s (1<s<N), and an amount of PPG data A2 of a group of people with high blood glucose is n (1<n<N), where s+n=N. Each piece of PPG data includes PPG signal information, a corresponding detection time (that is, a generation time of the PPG data, which may also be referred to as a timestamp), and a corresponding group of people type identifier.

In this implementation, a group of people type identifier of the PPG data A1 of the group of healthy people may be 0, and a group of people type identifier of the PPG data A2 of the group of people with high blood glucose may be 1. The group of people type identifier may be configured by the server 300 based on PPG data that is of a healthy user or a diabetic and that is reported by a user who reports PPG data.

The timestamp may be "sysTick": 1528962728. It may be determined, based on the timestamp (1528962728), that the generation time of the PPG data is xx (year)-xx (month)-xx (day) xx (hour): xx (minute): xx (second).

The PPG signal information may be, for example, "dataArray": [−133604, −132525, −131901, −133027, −135824]. The PPG signal information is reflected by an amplitude (for example, −133604 or −132525) of a PPG signal.

The initial PPG data includes N pieces of PPG data, and each piece of PPG data may be as follows:

[{"*sysTick*" : 1528962728, "*dataArray*" : [−133604, −132525, −131901, −133027, −135824], "*type*" : 1}, {...}, ...]

The PPG signal information in each piece of PPG data may be that five pieces of amplitude data form one group, and each piece of PPG data may include P groups of PPG signal information, that is, each piece of PPG data may include 5*P pieces of amplitude data.

P in PPG data may be the same or different.

Certainly, an amount of PPG signal information included in the PPG data may also be any other value, and may be determined based on a PPG data collection frequency. In addition, the PPG data may also be in another form.

S102: The mobile phone 100 obtains, from each of the PPG data A1 of the group of healthy people and the PPG data A2 of the group of people with high blood glucose, PPG data in two segments that is used to represent different blood glucose levels and uses the PPG data as difference adjustment data.

Because PPG data corresponding to a high blood glucose level and a low blood glucose level may be used to indicate a difference between blood glucose levels in terms of PPG, the mobile phone 100 may obtain, from each of the PPG data A1 of the group of healthy people and the PPG data A2 of the group of people with high blood glucose, the PPG data in the two segments that is used to represent the different blood glucose levels and use the PPG data as the difference adjustment data. The difference between the blood glucose levels in terms of the PPG can be mined, and blood glucose information in the PPG data can be amplified, by using the difference adjustment data, so that a problem that blood glucose information in a single piece of PPG data is weak can be resolved, and a classification effect is better.

In an implementation of this application, the mobile phone 100 obtains PPG data within a first time period from the PPG data A1 of the group of healthy people and uses the PPG data as first PPG data D1, where an amount of D1 is a ($1<a<s$). The first time period may be, for example, 03:00 to 04:00 at night, and a blood glucose level in a human body is usually low at night. Certainly, the first time period may also be a time period in which a blood glucose level in another human body is low at night.

The mobile phone 100 obtains PPG data within a second time period from the PPG data A1 of the group of healthy people and uses the PPG data as second PPG data D2, where an amount of D2 is b ($1<b<s$). The second time period may be, for example, 12:00 to 14:00 in the daytime, and a blood glucose level in a human body is usually high in the daytime. Certainly, the second time period may also be a time period in which a blood glucose level in another human body is high in the daytime.

In this implementation, a and b may be the same or different.

In addition, the mobile phone 100 obtains PPG data within the first time period from the PPG data A2 of the group of people with high blood glucose and uses the PPG data as third PPG data D3, where an amount of D3 is c ($1<c<n$). The mobile phone 100 obtains PPG data within the second time period from the PPG data A2 of the group of people with high blood glucose and uses the PPG data as fourth PPG data D4, where an amount of D4 is d ($1<d<n$).

In this implementation, c and d may be the same or different.

The difference adjustment data obtained by the mobile phone 100 includes four data sets: D1, D2, D3, and D4.

To enable the obtained blood glucose detection model to output a more accurate blood glucose detection result, a time interval between the first time period and the second time period needs to be greater than a time interval threshold. A value of the time interval threshold ranges from 4 hours to 10 hours, for example, may be 4 hours, 6 hours, 6.5 hours, 8 hours, or 10 hours, and may be set based on a requirement.

S103: The mobile phone 100 separately performs first data processing (or the first data processing may also be referred to as preprocessing) on PPG data in the four PPG data sets D1, D2, D3, and D4.

The first data processing includes data extraction processing, that is, PPG signal information is extracted from the PPG data, to obtain a data set of the PPG signal information.

The PPG signal information is represented by an amplitude of a PPG signal, and a data type of the PPG signal information is numeric. Numeric data (metric data) is a data type that indicates a quantity and that can be used for a numerical operation, and is represented as a specific value. For example, a data set of numeric PPG signal information on which first data processing is performed is [−133604, −132525, −131901, −+133027, −135824, . . . ].

After the data extraction processing is performed, if data items of the obtained PPG signal information are not unified, the data items of the obtained PPG signal information may be unified.

In addition, the first data processing may further include processing such as filtering processing, that is, filtering processing is performed on the PPG signal.

S104: The mobile phone 100 separately performs feature extraction on the PPG data that is in D1, D2, D3, and D4 and on which the first data processing is performed, to obtain a data set of feature data corresponding to D1, D2, D3, and D4, and performs average value calculation on the feature data to obtain an average value and use the average value as a difference adjustment value. The difference adjustment value may also be referred to as a baseline (baseline) value or difference adjustment feature data.

In an implementation of this application, the feature extraction may mean that the mobile phone 100 performs peak interval detection on the PPG data that is in D1, D2, D3, and D4 and on which the first data processing is performed, and calculates different types of T-dimensional features (T is a positive integer greater than 1) based on a peak interval. The T-dimensional features include a time-based feature (for example, a time feature such as a time feature corresponding to an amplitude or a time feature corresponding to a diastolic peak), a peak interval-based average value feature (for example, a peak interval-based feature is an RRI, which refers to an interval between two wave peaks, and a related average value feature is: calculating a primary difference and a secondary difference of an RRI sequence to obtain an average value feature such as an average value, a median value, and a minimum value of the RRI sequence), a standard deviation-based feature (for example, standard deviation of a valid RRI sequence), an entropy-based feature (for example, sample entropy, Shannon entropy, or approximate entropy), and a frequency-based feature (for example, LF (low frequency): a variation of a valid RRI in a range of 0.04 Hz to 0.15 Hz, or HF (high frequency): a variation of a valid RRI in a range of 0.15 Hz to 0.4 Hz), and the like. The T-dimensional features may be selected based on a requirement.

A method for performing feature extraction on the PPG data by the mobile phone 100 may be selected based on a requirement.

For example, the mobile phone 100 separately performs feature extraction on PPG data that is in D1 and on which first data processing is performed, obtains T-dimensional feature data having body feature information and uses the T-dimensional feature data as first PPG feature data $f_{i1}$ ($1 \le i \le a$), and calculates an average value of the first PPG feature data $f_{i1}$ and uses the average value as first difference adjustment value mf_D1.

Similarly, the mobile phone 100 separately performs feature extraction on PPG data that is in D2 and on which first data processing is performed, obtains T-dimensional feature data having body feature information and uses the T-dimensional feature data as second PPG feature data $f_{i2}$ ($1 \le i \le b$), and calculates an average value of the second feature data $f_{i2}$ and uses the average value as second difference adjustment value mf_D2.

The mobile phone 100 separately performs feature extraction on PPG data that is in D3 and on which first data processing is performed, obtains T-dimensional feature data having body feature information and uses the T-dimensional feature data as third PPG feature data $f_{i3}$ ($1 \le i \le c$), and calculates an average value of the third feature data $f_{i3}$ and uses the average value as third difference adjustment value mf_D3.

The mobile phone 100 separately performs feature extraction on PPG data that is in D4 and on which first data processing is performed, obtains T-dimensional feature data having body feature information and uses the T-dimensional feature data as fourth PPG feature data $f_{i4}$ ($1 \le i \le d$), and calculates an average value of the fourth feature data $f_{i4}$ and uses the average value as fourth difference adjustment value mf_D4.

mf_D1 is [mf1_D1, mf2_D1, ... , mfa_D1].

mf_D2 is [mf1_D2, mf2_D2, ... , mfb_D2].

mf_D3 is [mf1_D3, mf2_D3, ... , mfc_D3].

mf_D4 is [mf1_D4, mf2_D4, ... , mfd_D4].

A calculation formula of mf_D1 corresponding to each dimension of feature data $f_{i1}$ in D1 is as follows:

$$\text{mf\_1} = \text{baseline}(f_{i1}) = \frac{1}{a}\sum\nolimits_{j=1}^{a} f_{ji1}$$

A calculation formula of mf_D2 corresponding to each dimension of feature data $f_{i2}$ in D2 is as follows:

$$\text{mf\_D2} = \text{baseline}(f_{i2}) = \frac{1}{b}\sum\nolimits_{j=1}^{b} f_{ji2}$$

A calculation formula of mf_D3 corresponding to each dimension of feature data $f_{i3}$ in D3 is as follows:

$$\text{mf\_D3} = \text{baseline}(f_{i3}) = \frac{1}{c}\sum\nolimits_{j=1}^{c} f_{ji3}$$

A calculation formula of mf_D4 corresponding to each dimension of feature data $f_{i4}$ in D4 is as follows:

$$\text{mf\_D4} = \text{baseline}(f_{i4}) = \frac{1}{d}\sum\nolimits_{j=1}^{d} f_{ji4}$$

In this implementation, after obtaining the T-dimensional feature data corresponding to D1, D2, D3, and D4, the mobile phone 100 may further perform second data processing on the feature data, where the second data processing may be data cleaning. Performing data cleaning can improve quality of the T-dimensional feature data. Then, the mobile phone 100 obtains a corresponding difference adjustment value based on the T-dimensional feature data on which data cleaning is performed.

Performing data cleaning on the feature data includes checking data consistency to process an invalid value, a missing value, and the like. That is, data with poor data consistency, the invalid value, and the missing value can be removed. Certainly, data cleaning in another form may also be performed on the feature data.

In addition, a type of the feature data may also correspond to a numeric type, an enumeration type, or another type.

S105: The mobile phone 100 first performs feature extraction on each piece of PPG data in A1 and A2 that are included in the initial PPG data, to obtain initial PPG feature data corresponding to each piece of initial PPG data, and then learns through calculation that differences between the initial PPG feature data and mf_D1, mf_D2, mf_D3, and mf_D4 are respectively [fa–mf_D1, fa–mf_D2, fa–mf_D3, fa–mf_D4], where the differences are model training PPG feature data, and the differences are used as differences of feature information, and can bring more blood glucose information, to implement difference amplification processing on the initial PPG feature data.

$$fa - \text{mf\_D1} = f_i - \text{baseline}(f_{i1})$$

$$fa - \text{mf\_D2} = f_i - \text{baseline}(f_{i2})$$

$$fa - \text{mf\_D3} = f_i - \text{baseline}(f_{i3})$$

$$fa - \text{mf\_D4} = f_i - \text{baseline}(f_{i4})$$

$f_i$ is the initial PPG feature data corresponding to the initial PPG data, and $1<i<N$. Therefore, it is learned that the differences between the initial PPG feature data and mf_D1, mf_D2, mf_D3, and mf_D4 respectively include the following four data sets:

$$[f1 - \text{mf1\_D1},\ f2 - \text{mf2\_D1},\ \dots,\ fN - \text{mfa\_D1}]$$

$$[f1 - \text{mf1\_D2},\ f2 - \text{mf2\_D2},\ \dots,\ fN - \text{mfb\_D2}]$$

$$[f1 - \text{mf1\_D3},\ f2 - \text{mf2\_D3},\ \dots,\ fN - \text{mfc\_D3}]$$

$$[f1 - \text{mf1\_D4},\ f2 - \text{mf2\_D4},\ \dots,\ fN - \text{mfb\_D4}]$$

In this case, the model training PPG feature data determined by the mobile phone 100 is a data set including the foregoing four difference sets, and is specifically [f1–mf1_D1, f2–mf2_D1, . . . , fN–mfa_D1, f1–mf1_D2, f2–mf2_D2, . . . , fN–mfb_D2, f1–mf1_D3, f2–mf2_D3, . . . , fN–mfc_D3, f1–mf1_D4, f2–mf2_D4, . . . , fN–mfd_D4].

S106: The mobile phone 100 marks the model training PPG feature data based on a group of people type label, and trains and optimizes the model training PPG feature data by using a machine learning model, to obtain a blood glucose detection model.

For example, a group of people type label corresponding to the PPG data A1 of the group of healthy people is 0, and a group of people type label corresponding to the PPG data of the group of people with high blood glucose is 1. A group of people type label of the obtained model training PPG feature data is consistent with a group of people type label of the corresponding initial PPG data. That is, in the model training PPG feature data, a group of people type label of feature data of a group of healthy people is 0, and a group of people type label of feature data of a group of people with high blood glucose is 1.

Certainly, the group of people type label may also be, for example, another label such as a digit, a letter, or a symbol, and may be selected based on a requirement.

The machine learning model may be, for example, XGBoost, or may be another machine learning model such as lightGBM. A specific training process of the machine learning model is not described in detail in this application, and may be selected based on a requirement.

The blood glucose detection model is an algorithm model, and may be referred to as a classifier. More blood glucose features may be obtained through difference mining by using a machine learning method.

The blood glucose detection model may perform high blood glucose risk probability calculation on to-be-measured PPG feature data that is input into the blood glucose detection model and that is used as input data, to obtain a high blood glucose risk probability value used as an output result, so as to screen for a high blood glucose risk and monitor a blood glucose status of a user. In this implementation, the blood glucose detection model may also be referred to as a high blood glucose risk screening model.

In another implementation of this application, step S101 in which the mobile phone 100 obtains the initial PPG data from the server 300 may alternatively be as follows: Each time the mobile phone 100 detects an operation of opening a blood glucose detection application by a user, the mobile phone 100 sends an initial PPG data obtaining request to the server 300 to obtain the initial PPG data.

In another implementation of this application, step S101 in which the mobile phone 100 obtains the initial PPG data from the server 300 may alternatively be as follows: The mobile phone 100 may periodically obtain the initial PPG data based on a preset model training period, and periodically perform model training to update the blood glucose detection model, so that a detection result output by the blood glucose detection model can be more accurate. The model training period may be one week, one month, or any other time, and may be selected based on a requirement.

A fixed model training period may be configured in the blood glucose detection application in the mobile phone 100. Certainly, the blood glucose detection application may also provide a model training period setting control, so that the user sets a model training period.

Certainly, the mobile phone 100 may also obtain the initial PPG data in another case based on a requirement.

In another implementation of this application, step S102 in which the mobile phone 100 obtains, from each of the PPG data A1 of the group of healthy people and the PPG data A2 of the group of people with high blood glucose, PPG data in two segments that is used to represent different blood glucose levels and uses the PPG data as the difference adjustment data may alternatively be as follows: The mobile phone 100 obtains PPG data within a first value range from the PPG data of the group of healthy people and uses the PPG data as first PPG data D1, and obtains PPG data within a second value range from the PPG data of the group of healthy people and uses the PPG data as second PPG data, where a blood glucose level represented by the first value range is lower than a blood glucose level represented by the second value range; and obtains PPG data within a third value range from the PPG data of the group of people with high blood glucose and uses the PPG data as third PPG data D3, and obtains PPG data within a fourth value range from the PPG data of the group of people with high blood glucose and uses the PPG data as fourth PPG data D4, where a blood glucose level represented by the third value range is lower than a blood glucose level represented by the fourth value range. The mobile phone 100 uses the first PPG data, the second PPG data, the third PPG data, and the fourth PPG data as the difference adjustment data.

A value range may be a value range of an amplitude of the PPG data, and the first value range, and the second value range, the third value range, and the fourth value range may be selected based on a requirement.

In another implementation of this application, the mobile phone 100 may alternatively obtain, from each of the PPG data A1 of the group of healthy people and the PPG data A2 of the group of people with high blood glucose, PPG data in a plurality of segments (for example, three segments, four segments, or eight segments) that is used to represent different blood glucose levels and use the PPG data as the difference adjustment data; and obtain difference adjustment values based on the difference adjustment data to adjust the initial PPG feature data, so as to obtain a blood glucose detection model that can output a more accurate blood glucose detection result.

In another implementation of this application, the mobile phone 100 may also directly obtain D1, D2, D3, and D4 from the server 300, where D1, D2, D3, and D4 are determined by the server 300 from a plurality of pieces of stored PPG data. A process of determining D1, D2, D3, and D4 is the same as a process of determining D1, D2, D3, and D4 by the mobile phone 100. Details are not described herein again.

In another implementation of this application, the mobile phone 100 may also calculate sums of the initial PPG feature data and the difference adjustment values, and obtain the model training PPG feature data based on the sums of the initial PPG feature data and the difference adjustment values.

Certainly, the mobile phone 100 may also perform another type of calculation on the initial PPG feature data and the difference adjustment values, for example, setting an adjustment coefficient (the adjustment coefficient may be any value other than 1 such as 0.5, 1.2, or 2), calculating a product, or calculating a quotient, to obtain the model training PPG feature data. The calculation may be selected based on a requirement.

In this implementation, the mobile phone 100 obtains, from each of the PPG data A1 of the group of healthy people and the PPG data A2 of the group of people with high blood glucose, the PPG data used to represent the different blood glucose levels (a high blood glucose level and a low blood glucose level) and uses the PPG data as the difference adjustment data; obtains the difference adjustment values based on the difference adjustment data; performs difference amplification processing on the initial PPG feature data based on the difference adjustment values, to obtain the model training PPG feature data; and obtains the blood glucose detection model based on the model training PPG feature data. Compared with a manner in which feature extraction is directly performed on initial PPG data and model training is performed to generate a blood glucose detection model, a manner in which blood glucose information in the PPG data can be amplified differently by using the difference adjustment data resolves problems that the blood glucose information in the PPG data is weak and extraction of blood glucose-related features is difficult. Therefore, according to the PPG-based blood glucose detection method provided in this application, the blood glucose detection result output by the obtained blood glucose detection model can be more accurate. That is, when high blood glucose screening is performed, a screening result can be more accurate.

Figure 4B:
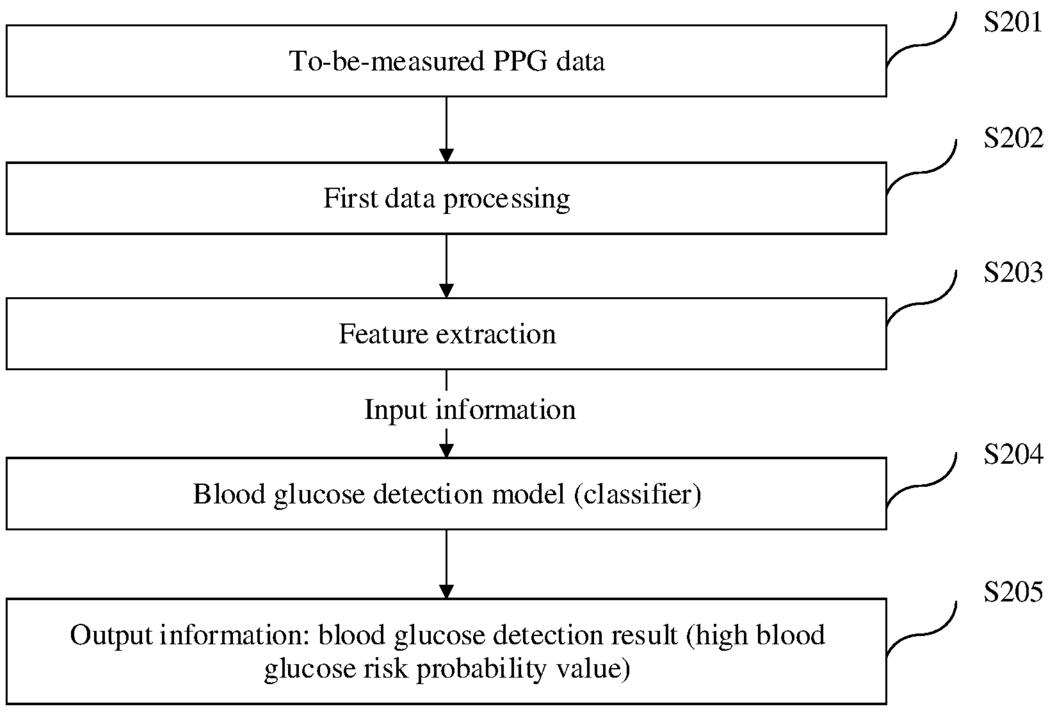
FIG. 4B is a schematic flowchart of a blood glucose detection method according to some implementations of this application.

Refer to FIG. 4B. In an implementation of the blood glucose detection method provided in this application, a process in which the mobile phone 100 performs blood glucose detection includes the following steps.

S201: The mobile phone 100 obtains to-be-measured PPG data when the mobile phone 100 detects a blood glucose detection instruction of a user.

The band 200 automatically performs PPG detection based on a preset detection period to obtain PPG data, where the detection period may be any value such as 1 minute, 5 minutes, or 10 minutes.

Then, when establishing a communication connection to the mobile phone 100, the band 200 synchronizes the PPG data obtained through detection to the mobile phone. After the mobile phone 100 detects the blood glucose detection instruction of the user, the mobile phone 100 may obtain the PPG data from the mobile phone 100 and use the PPG data as the to-be-measured PPG data.

The to-be-measured PPG data may be one piece of PPG data, or may be a plurality of pieces of PPG data within a period of time (for example, 3 s or 5 s).

S202: The mobile phone 100 performs first data processing on the to-be-measured PPG data.

S203: The mobile phone 100 performs feature extraction on the to-be-measured PPG data on which the first data processing is performed, to obtain to-be-measured PPG feature data.

Processes in which the mobile phone 100 performs the first data processing and the feature extraction on the to-be-measured PPG data are respectively similar to steps S103 and S104. Details are not described herein again.

S204: The mobile phone 100 inputs the to-be-measured PPG feature data into a pre-trained blood glucose detection model.

S205: The mobile phone 100 obtains a blood glucose detection result used as an output result of the blood glucose detection model.

The blood glucose detection method provided in this implementation may be used for high blood glucose risk screening, that is, may be referred to as a high blood glucose risk screening method. In this case, the blood glucose detection result may be a high blood glucose risk screening result, and the blood glucose detection result may be a high blood glucose risk probability value.

After obtaining the blood glucose detection result, the mobile phone 100 may generate blood glucose detection information corresponding to the blood glucose detection result, and display the blood glucose detection information in an interface of the mobile phone 100 for viewing by a user. The blood glucose detection information includes high blood glucose risk level information and user reminder information.

The high blood glucose risk level information may be a plurality of types of high blood glucose risk level information determined based on the high blood glucose risk probability value, for example, may be a high risk, a medium risk, and a low risk.

The user reminder information may include information such as a time point at which the user performs blood glucose detection, a quantity of blood glucose detection times, a quantity of times that a quantity of high-risk times exceeds a security threshold, and information used to perform health intervention on the user. The information used to perform health intervention on the user includes suggestion information such as a time for suggesting the user perform blood glucose detection, and a diet and exercise of the user. Health intervention or auxiliary intervention can be performed on the user to implement functions of non-invasive and continuous monitoring for a high blood glucose risk status of the user.

In addition, after obtaining the blood glucose detection result, the mobile phone 100 may further collect statistics about a quantity of times of high risks caused by blood glucose within a preset time period. If the quantity of high-risk times exceeds a security threshold, the mobile phone generates first notification information, and sends the first notification information to an associated device corresponding to an associated person. If the quantity of high-risk times is less than a security threshold, the mobile phone generates second notification information, and sends the second notification information to an associated device corresponding to an associated person.

The first notification information may be "Hello, a high blood glucose risk of the user XXX has been continuously found through screening for a plurality of times. Please pay attention to the risk in a timely manner!". The second notification information may be "Hello, a high-risk situation of the user XXX has been improved currently". Certainly, the first notification information and the second notification information may alternatively be other information.

The first notification information and the second notification information may be information pre-configured in a blood glucose detection application. Certainly, the blood glucose detection application may also provide a notification information setting control, so that the user enters notification information by using the mobile phone 100, to set the notification information.

In another implementation of this application, the band 200 may alternatively store PPG data obtained by the band 200 through detection. Step S201 in which the mobile phone 100 obtains the to-be-measured PPG data may alternatively be as follows: The mobile phone 100 sends a to-be-measured PPG data obtaining request to the band 200 after the mobile phone 100 detects a blood glucose detection instruction of the user. After receiving the to-be-measured PPG data obtaining request, the band 200 sends the to-be-measured PPG data to the watch 100.

In addition, when detecting that the user opens the blood glucose detection application, the mobile phone 100 may also send a to-be-measured PPG data obtaining request to the band 200, to obtain the to-be-measured PPG data.

The blood glucose detection method provided in this implementation is a non-invasive blood glucose detection method. During blood glucose detection, the mobile phone 100 may input, into a pre-trained blood glucose detection model, the to-be-measured PPG data obtained by the band 200 through detection, so that non-invasive blood glucose detection can be conveniently and quickly implemented.

In addition, the mobile phone 100 depends only on the PPG data obtained by the band 200, and does not depend on other data, so that noise data can be reduced. According to the blood glucose detection method provided in this implementation, an obtained blood glucose detection result can be more accurate.

In addition, compared with the non-invasive blood glucose detection method provided in the conventional technology, in this method, the PPG data is easily obtained, so that the blood glucose detection method provided in this implementation can meet a requirement of a user for daily non-invasive screening for diabetes.

The mobile phone 100 obtains a blood glucose detection model by using a machine learning method, and automatically or actively performs high blood glucose risk screening on the user, so that continuous and non-invasive screening for high blood glucose and monitoring for a high blood glucose risk status of the user can be implemented, and an intervention suggestion can be made for the user, which is conducive to prevention and control of high blood glucose, and can improve user experience.

In addition, in this implementation, the mobile phone 100 may generate blood glucose detection information based on a blood glucose detection result for viewing by the user and a related person. Therefore, the user can intervene in advance on the basis of detecting blood glucose of the user, so that the user pays attention to blood glucose screening, a diet, exercise, and the like, to improve user experience.

In this implementation, the blood glucose detection result may be a high blood glucose risk probability value, or may be other information that may be used to indicate a high blood glucose risk screening result.

Figure 5:
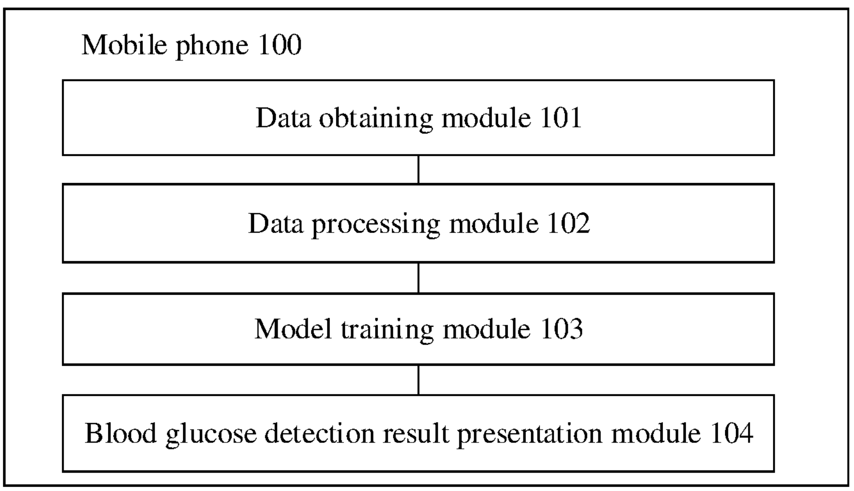
FIG. 5 is another schematic diagram of a structure of a mobile phone 100 according to some implementations of this application.

FIG. 5 is another schematic diagram of a structure of an example mobile phone 100 according to an embodiment of this application.

The mobile phone 100 includes a data obtaining module 101, a data processing module 102, a model training module 103, and a blood glucose detection result presentation module 104. The data obtaining module 101 is configured to: store initial PPG data obtained from the server 300, and store to-be-measured PPG data obtained from the band 200. The data processing module 102 is configured to process the initial PPG data to obtain the foregoing model training PPG feature data. The model training module 103 is configured to perform model training based on the model training PPG feature data, to obtain a blood glucose detection model. The data processing module 102 is further configured to perform feature extraction on the to-be-measured PPG data to obtain to-be-measured PPG feature data. The blood glucose detection result presentation module 104 is configured to present a blood glucose detection result obtained after the to-be-measured PPG feature data is input into the blood glucose detection model obtained by the model training module 103.

For a specific data processing process of the data obtaining module 101, the data processing module 102, the model training module 103, and the blood glucose detection result presentation module 104, refer to steps S101 to S106, and steps S201 to S205. Details are not described herein again.

In addition, in this application, the server 300 may include a PPG data collection module (not shown in the figure). The PPG data collection module is configured to: collect and store PPG data.

The blood glucose detection method provided in this application may be used to perform high blood glucose risk screening, and an obtained blood glucose detection result may also be referred to as a high blood glucose risk screening result.

Figure 6A:
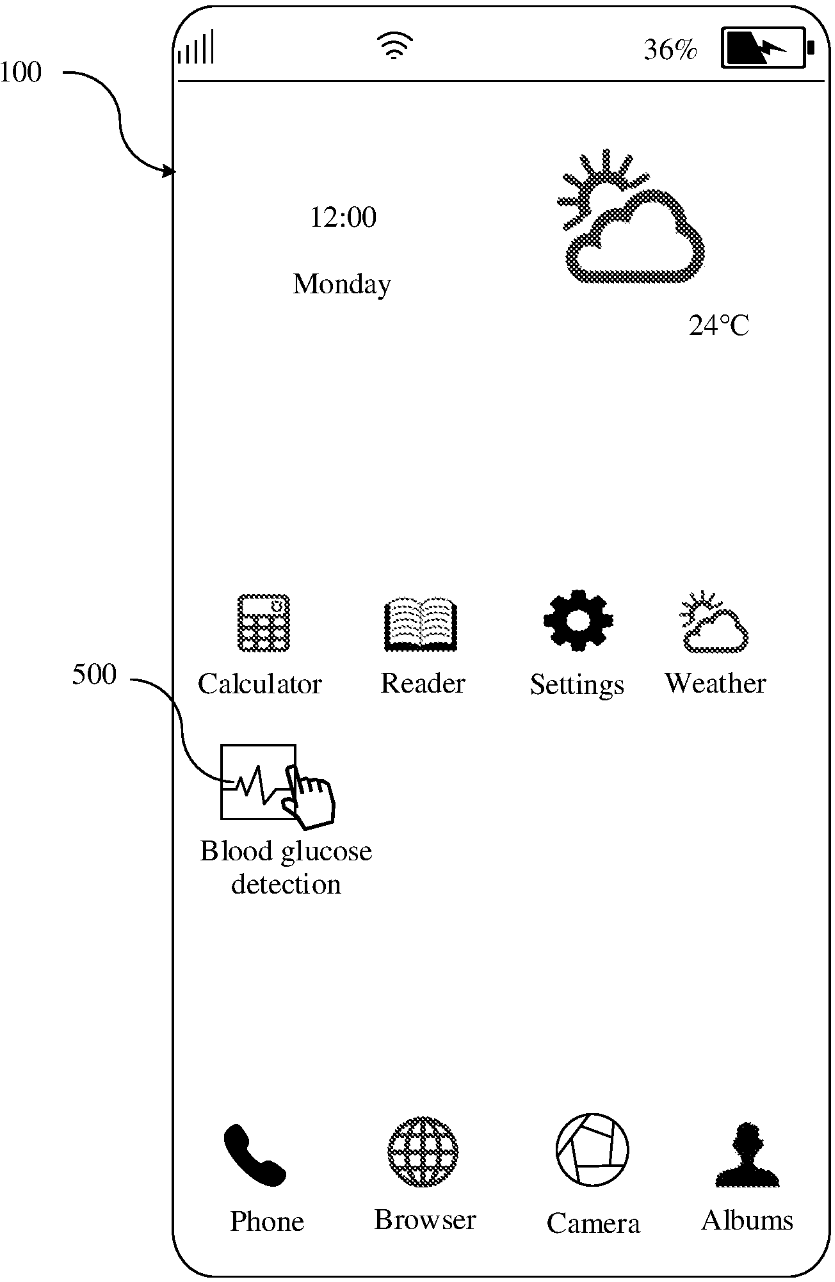
FIG. 6A to FIG. 6H are schematic diagrams of some interfaces of a mobile phone 100 and a mobile phone 600 according to some implementations of this application.

Refer to FIG. 6A. In another implementation of the blood glucose detection method provided in this application, the mobile phone 100 includes a blood glucose detection application 500. If the mobile phone 100 detects a trigger operation (or may be referred to as a tap operation) performed by a user on the blood glucose detection application 500, the mobile phone 100 opens the blood glucose detection application 500, and displays an interface shown in FIG. 6B.

The interface includes a "Home page" control 501, a "Discover" control 502, and a "Me" control 503. The mobile phone 100 displays, by default, an interface corresponding to the "Home page" control 501. The interface corresponding to the "Home page" control 501 includes a first display area 510, and the first display area 510 is a status description area of "High blood glucose risk screening".

The first display area 510 includes a "Start" control 511. If the mobile phone 100 detects a trigger operation performed by the user on the "Start" control 511, the mobile phone 100 obtains to-be-measured PPG data, and obtains a blood glucose detection result based on the to-be-measured PPG data.

In addition, in another implementation of this application, that the mobile phone 100 obtains to-be-measured PPG data may alternatively be as follows: The mobile phone 100 obtains the to-be-measured PPG data from the band 200 when the mobile phone 100 detects a trigger operation performed by the user on the blood glucose detection application 500. When the mobile phone 100 detects the trigger operation performed by the user on the "Start" control 511, the mobile phone 100 directly obtains a blood glucose detection result based on the to-be-measured PPG data.

The first display area 510 further includes first user reminder information 512, and the first user reminder information 512 is used to remind the user of a high blood glucose risk screening status on a current day. For example, the first user reminder information 512 displays "High blood glucose risk screening has not been performed today".

The first display area 510 further includes second user reminder information 513, and the second user reminder information 513 is used to display description information such as "This detection is not used as a professional clinical diagnosis basis for high blood glucose".

The interface corresponding to the "Home page" control 501 further includes a second display area 520, and the second display area 520 is a status description area of "Screening statistics". The second display area 520 includes screening statistics information used as user reminder information.

The screening statistics information includes a quantity of blood glucose detection times and a quantity of times that a quantity of high-risk times exceeds a security threshold. The quantity of blood glucose detection times may be, for example, a quantity 521 of screening times in this month, and the quantity of times that the quantity of high-risk times exceeds the security threshold may be, for example, a quantity 522 of high-risk times in this month.

The screening statistics information further includes third user reminder information 523, and the third user reminder information 523 may be "High blood glucose risk screening has not been performed this month, and it is recommended to perform screening at least once a week".

Figure 6B:
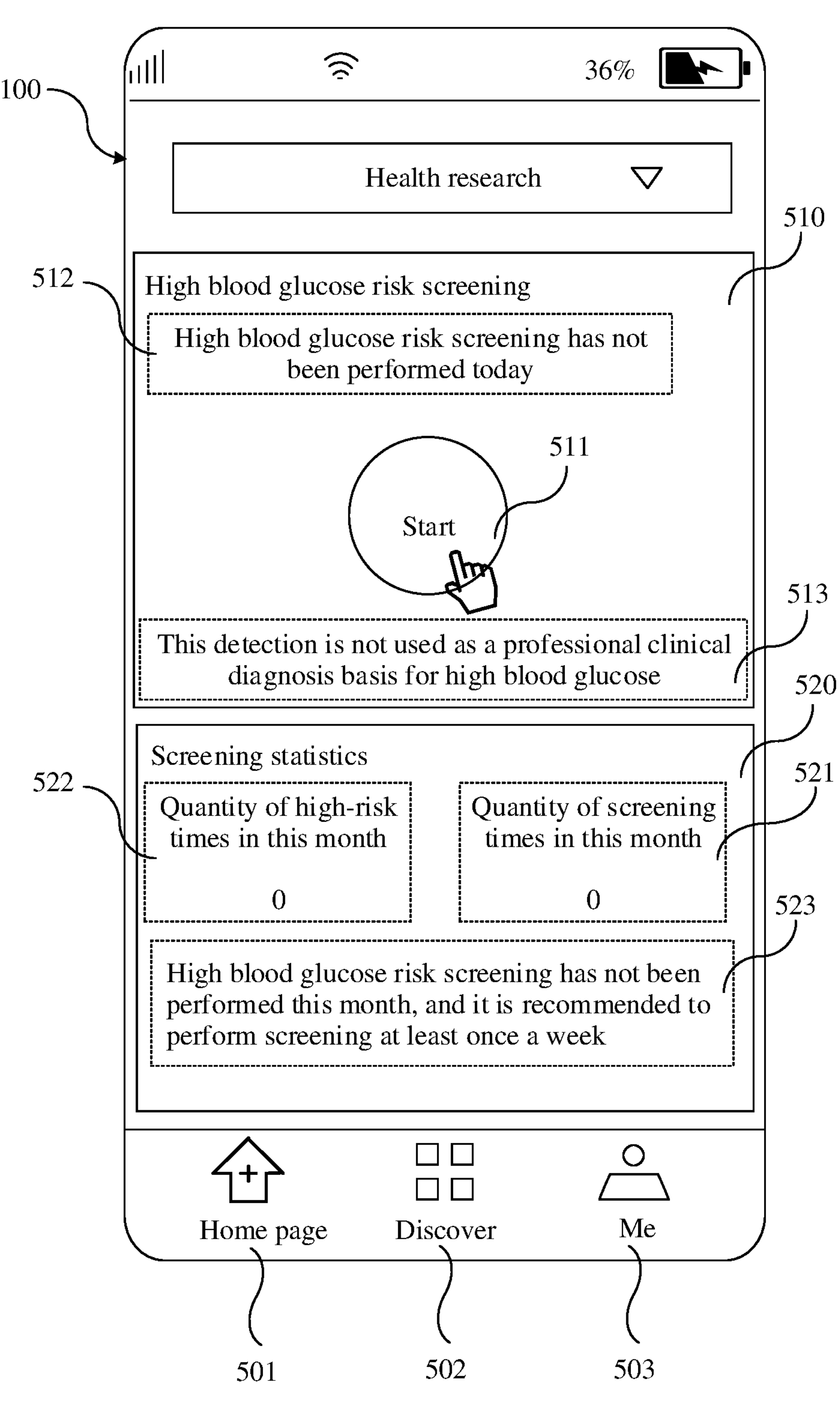
Figure 6C:
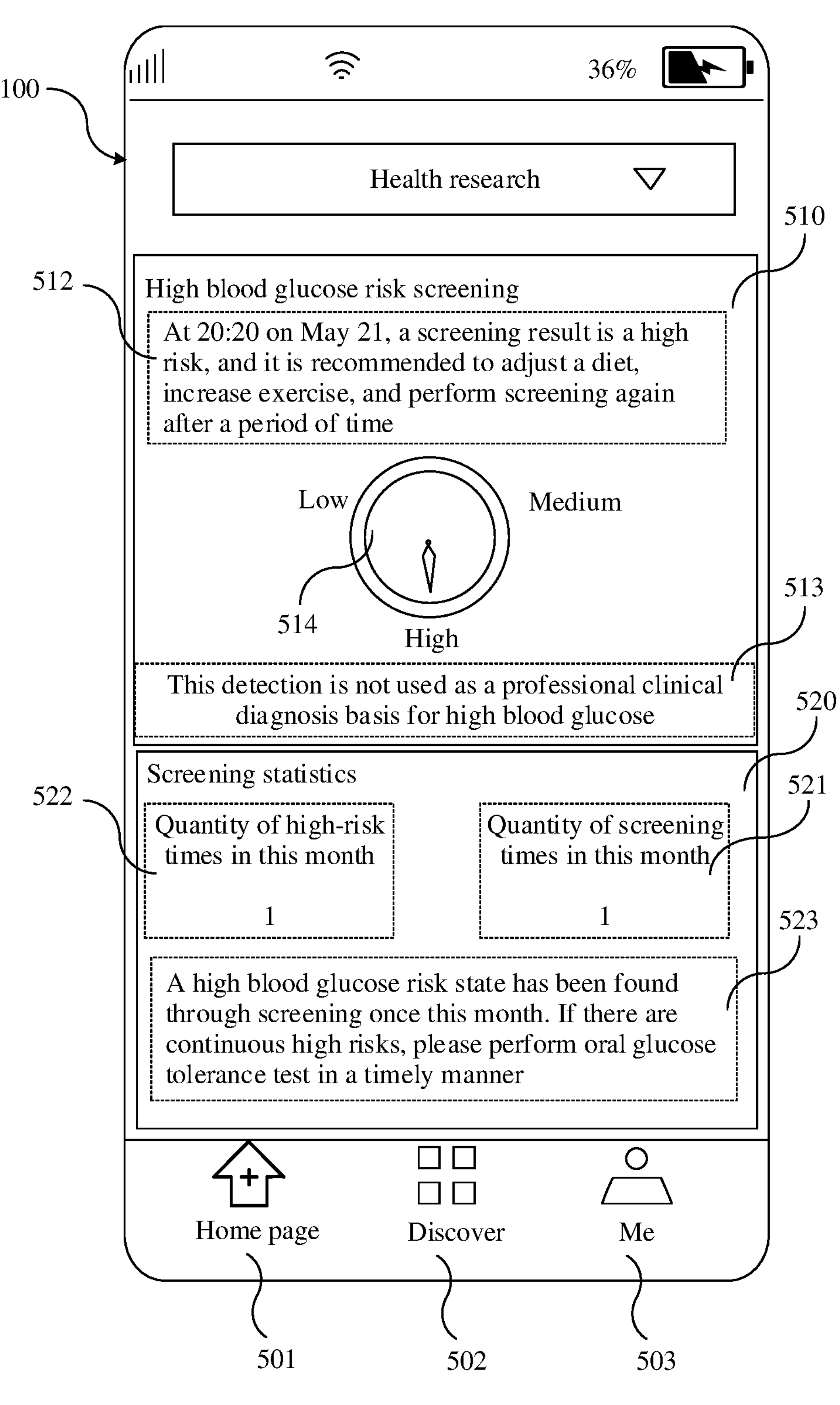

After obtaining a high blood glucose risk screening result, the mobile phone 100 may display an interface shown in FIG. 6C. In this case, the first display area 510 displays high blood glucose risk screening result information. The high blood glucose risk screening result information includes a high blood glucose risk level, and the high blood glucose risk level may be represented by a risk level ring marked with words "High", "Medium", and "Low", to represent different risk levels. A location indicated by an arrow is a high blood glucose risk level obtained in this detection. As shown in FIG. 6C, a high blood glucose risk level obtained in this detection is "High".

The mobile phone 100 presents three risk levels: High, Medium, and Low to the user in an interface, so that the user can intuitively view the risk levels.

In addition, the mobile phone 100 updates the first user reminder information 512 based on the high blood glucose risk screening result. The first user reminder information 512 is updated to information including a current detection time, a screening result, and suggestion information. For example, the first user reminder information 512 is updated to "At 20:20 on May 21, a screening result is a high risk, and it is recommended to adjust a diet, increase exercise, and perform screening again after a period of time".

In addition, the mobile phone 100 updates, based on the high blood glucose risk screening result, the screening statistics information included in the second display area 520. The quantity 522 of high-risk times in this month is updated to "1", and the quantity of screening times in this month is updated to "1".

The mobile phone 100 updates the third user reminder information 523 based on the high blood glucose risk screening result, where the third user reminder information 523 is updated to "A high blood glucose risk state has been found through screening once this month. If there are continuous high risks, please perform oral glucose tolerance test in a timely manner".

Figure 6D:
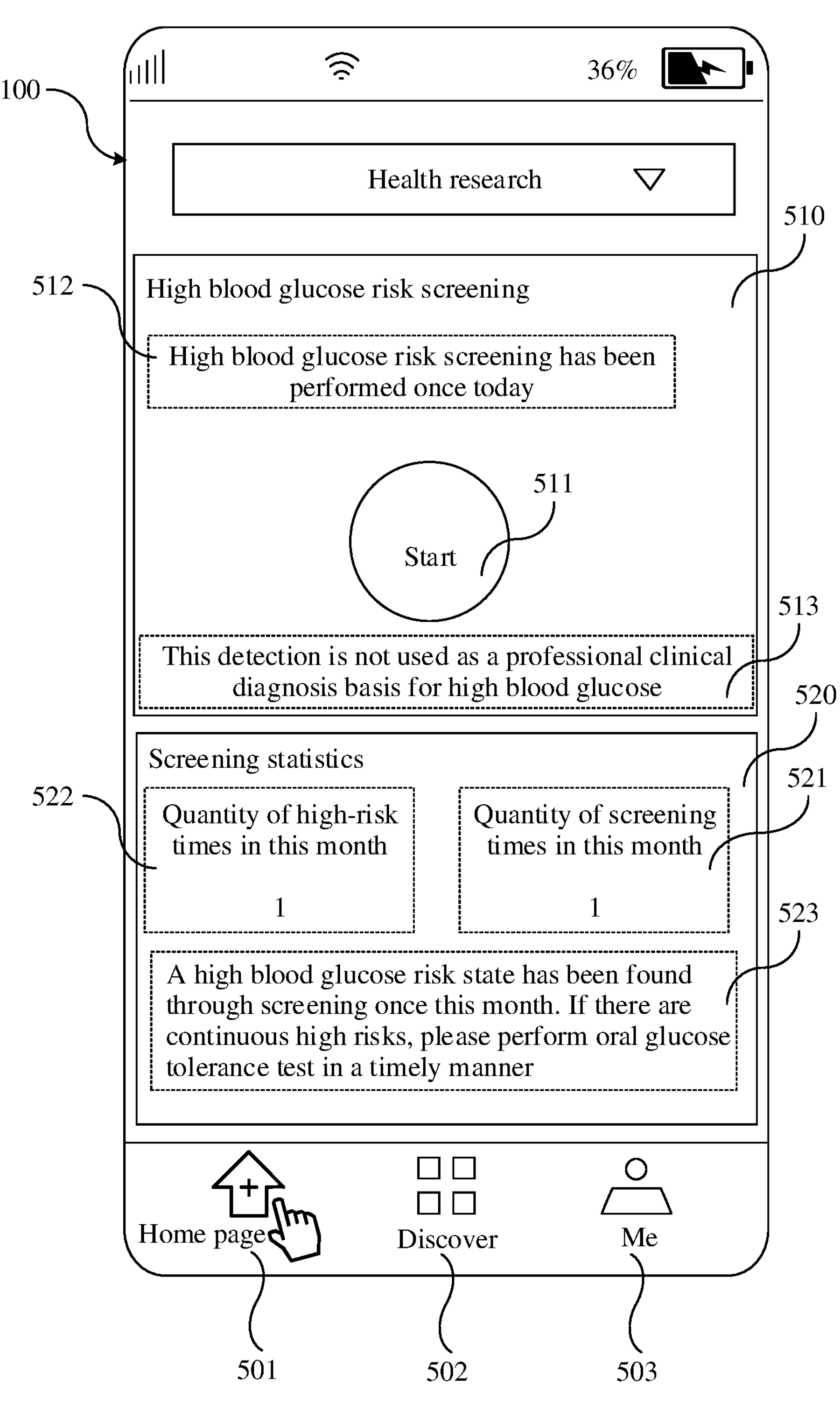

If the mobile phone 100 detects a trigger operation performed by the user on the "Home page" control 501, the mobile phone 100 refreshes the interface, and displays an interface shown in FIG. 6D. In this case, the first display area 510 of the mobile phone 100 displays a "Start" control 511, and the user may tap the "Start" control 511 to perform high blood glucose risk screening again. In addition, the first user reminder information 512 is updated to "High blood glucose risk screening has been performed once today".

Certainly, the mobile phone 100 may also provide, in the interface shown in FIG. 6C, a back control used by the user to perform a back operation. If the mobile phone 100 detects a trigger operation performed by the user on the back control, the mobile phone 100 updates the interface shown in FIG. 6C to the interface shown in FIG. 6D.

In this implementation, after a quantity of high-risk times in this month exceeds a security threshold, the mobile phone 100 may send first notification information to an associated device corresponding to a related associated person. The associated person may be a relative or a friend of the user, a doctor, or the like, and may be set by the user. The associated device may be a mobile phone, a computer, or a patient condition detection server in a hospital, to record a user condition, so that a doctor can view the user condition. The mobile phone 100 may send the first notification information to the associated device by using an SMS message, or may send the first notification information by using an associated application (for example, the blood glucose detection application 500 is also installed on the associated device), or may send the first notification information in any other manner, which may be set based on a requirement.

Figures 1, 6E:
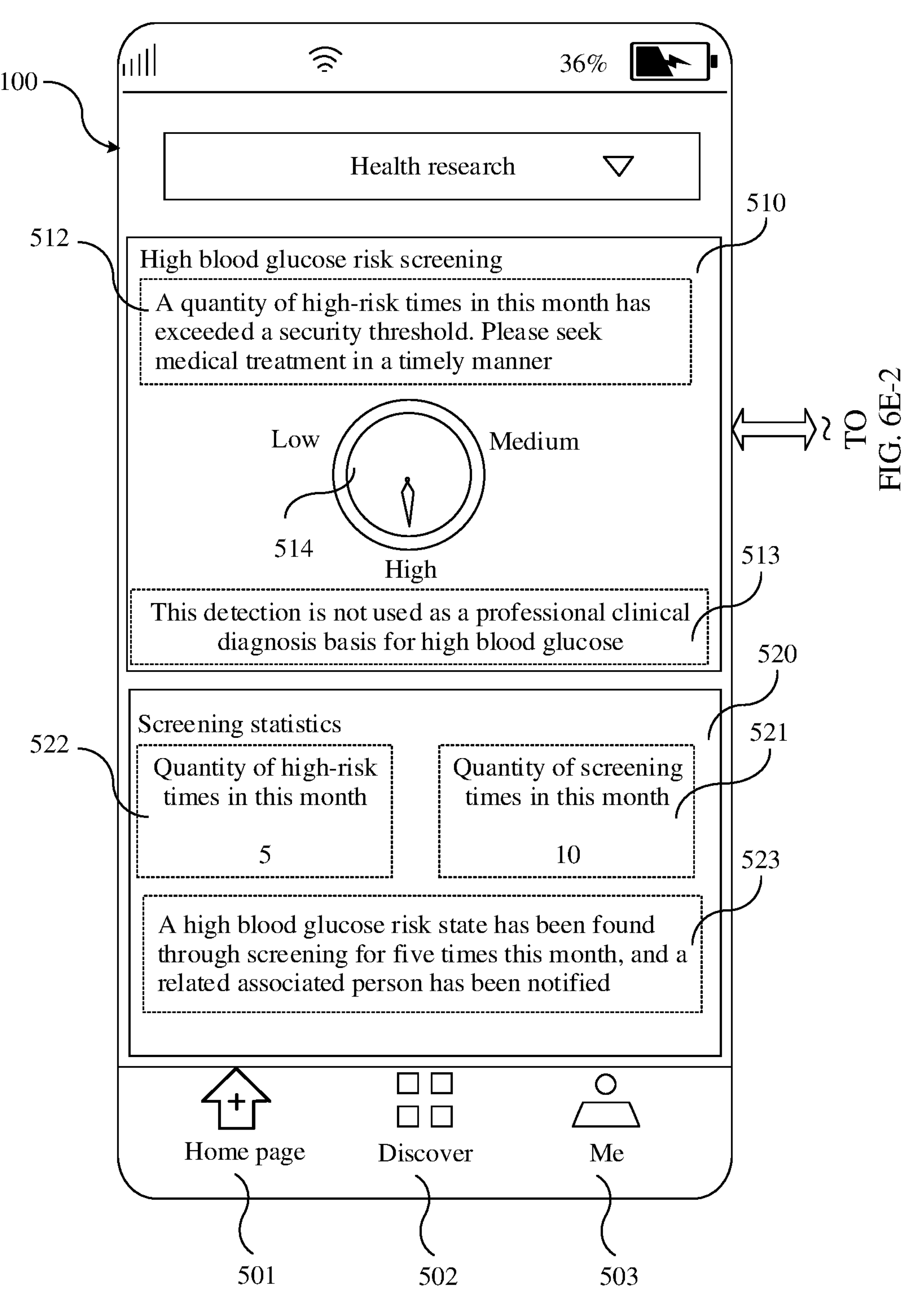
Figures 2, 6E:
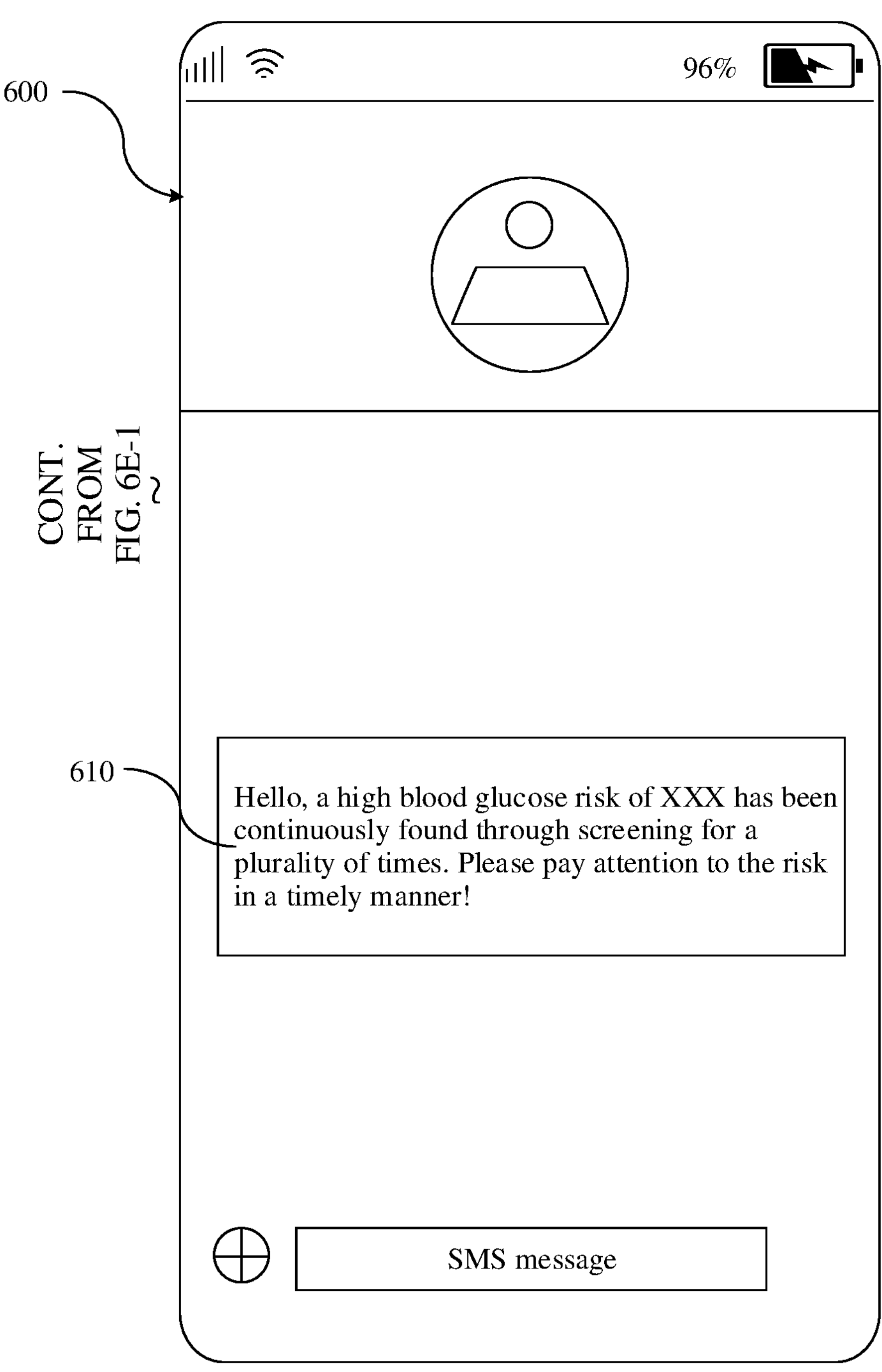

As shown in FIG. 6E-1 and FIG. 6E-2, the associated device may be a mobile phone 600. First notification information that is sent by the mobile phone 100 and that is received by the mobile phone 600 may be "Hello, a high blood glucose risk of XXX has been continuously found through screening for a plurality of times. Please pay attention to the risk in a timely manner!".

After the mobile phone 100 sends the first notification information to the mobile phone 600 by using an SMS message, the mobile phone 100 displays an interface shown in FIG. 6E-1 and FIG. 6E-2. The third user reminder information 523 is updated to "A high blood glucose risk state has been found through screening for five times this month, and a related associated person has been notified".

Figures 1, 6F:
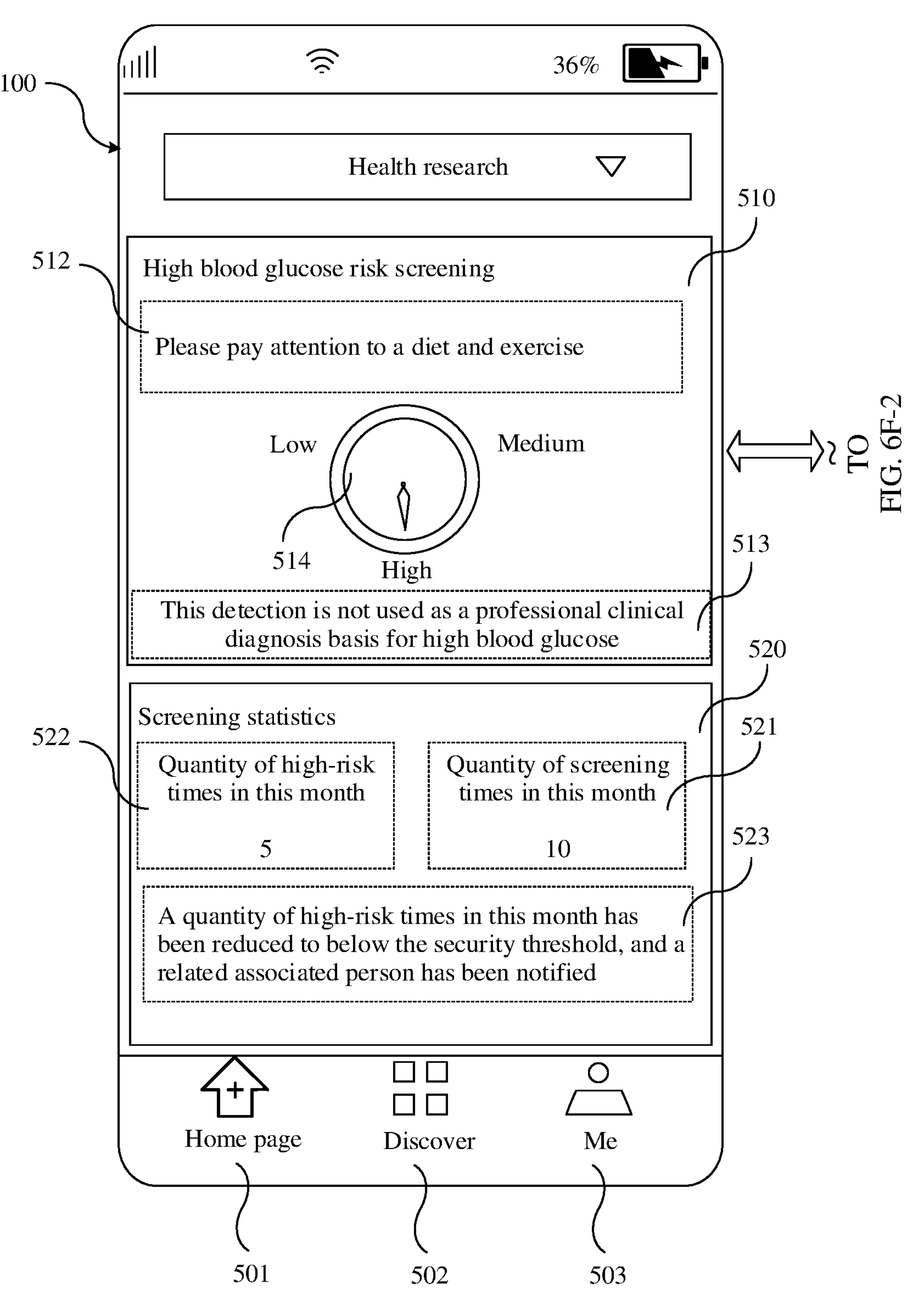
Figures 2, 6F:
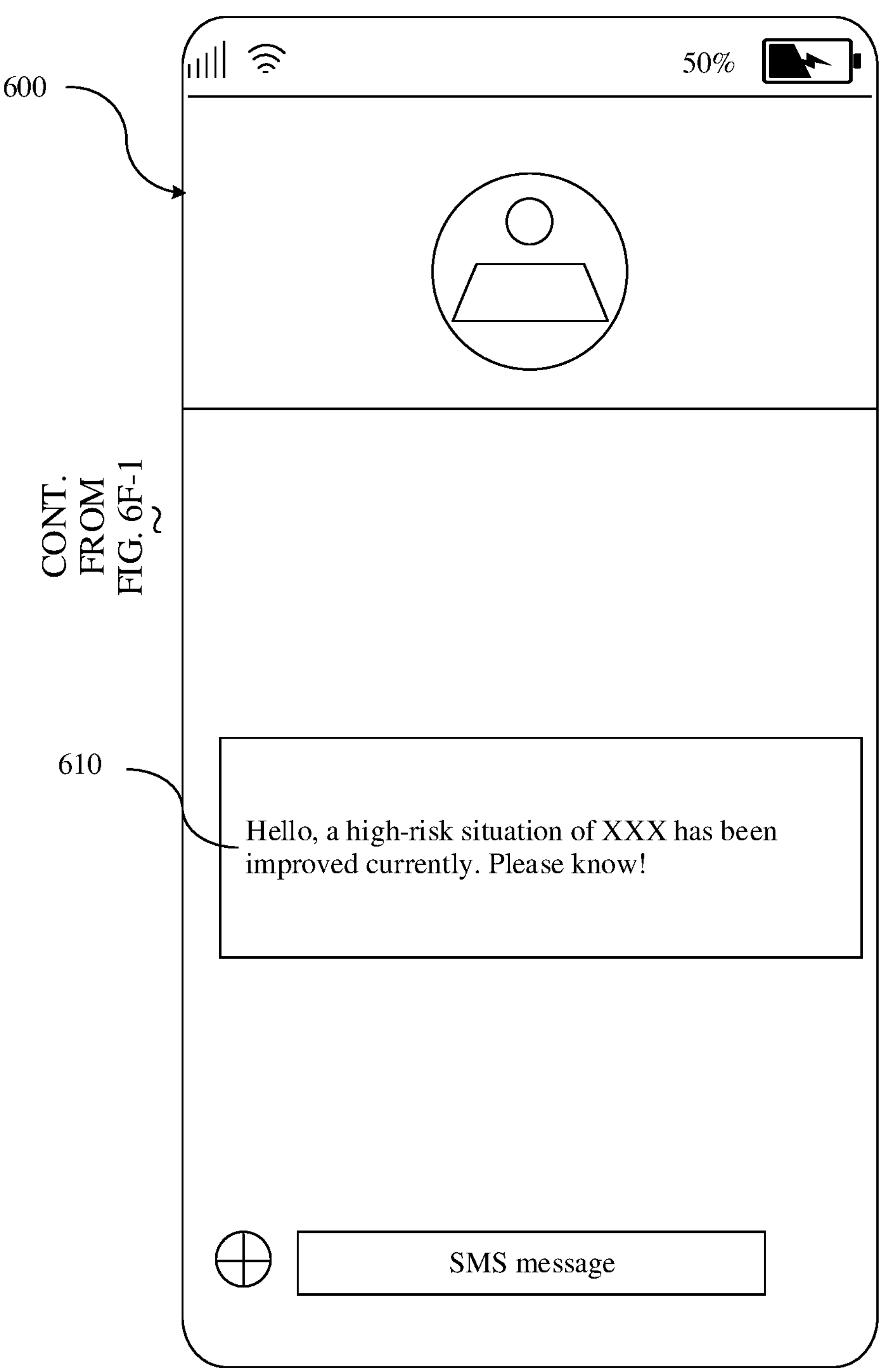

In addition, after the user condition is improved, for example, the mobile phone 100 detects that the quantity of high-risk times is less than the security threshold within a preset time period (for example, within one week after the security threshold is exceeded), the mobile phone 100 sends second notification information to the mobile phone 600 by using an SMS message. As shown in FIG. 6F-1 and FIG. 6F-2, the second notification information may be "Hello, a high-risk situation of XXX has been improved currently".

After the mobile phone 100 sends the second notification information to the mobile phone 600, the mobile phone 100 displays an interface shown in FIG. 6F-1 and FIG. 6F-2. The third user reminder information 523 is updated to "A quantity of high-risk times in this month has been reduced to below the security threshold, and a related associated person has been notified".

In this implementation, the mobile phone 100 may provide different health intervention suggestions based on the high blood glucose risk screening result, the quantity of high-risk times, and different cases. That is, in this implementation, content of the first user reminder information 512, the second user reminder information 513, and the third user reminder information 523 is updated with a user operation and a high blood glucose risk screening result.

Figure 6G:
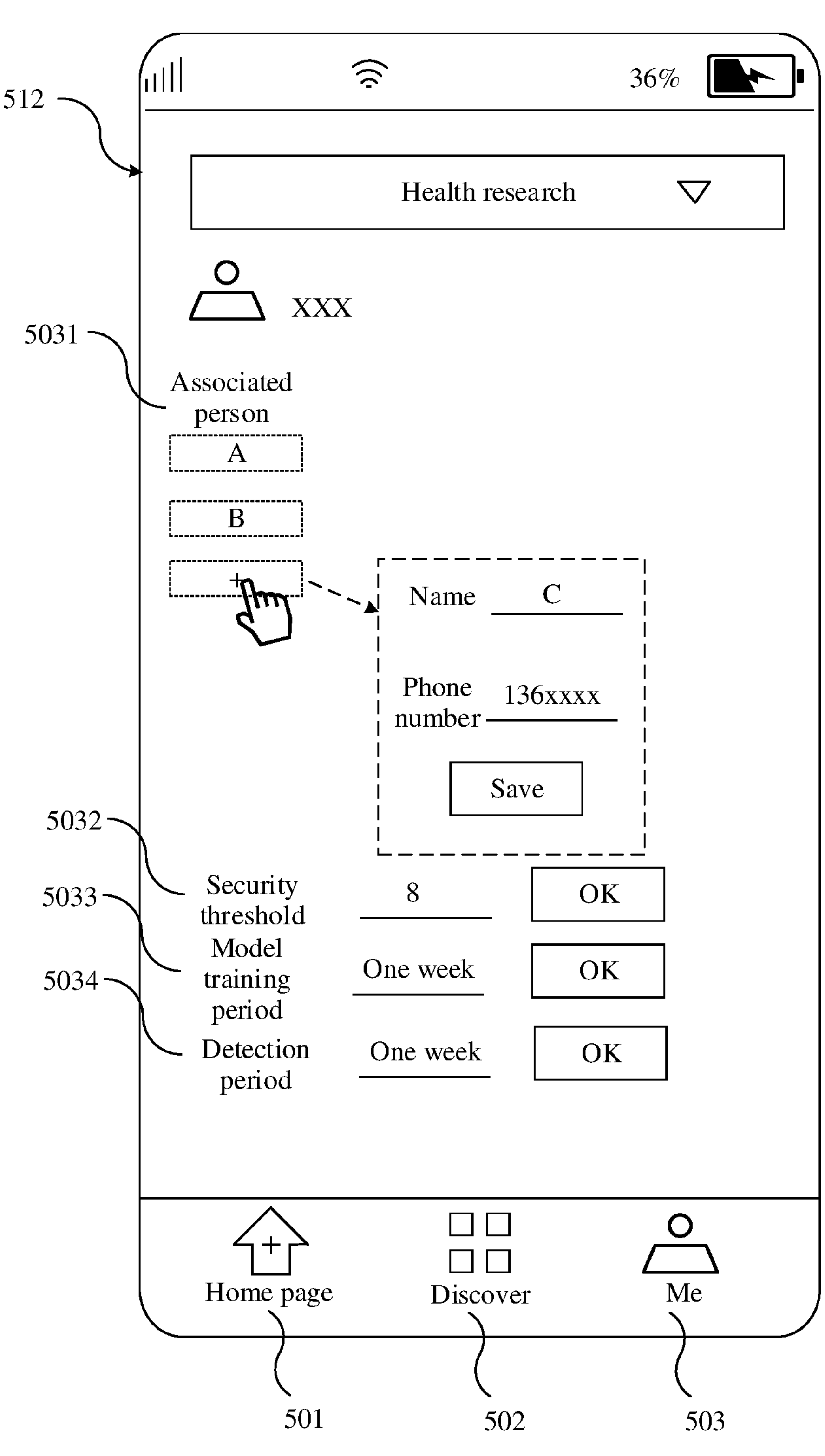

In addition, in this implementation, the user may tap the "Me" control 503 to set an associated person. If the mobile phone 100 detects a trigger operation performed by the user on the "Me" control 503, the mobile phone 100 displays an interface shown in FIG. 6G. The interface includes an "Associated person" setting control 5031. The user can set a name, phone number, and the like of the associated person by using the "Associated person" setting control 5031.

In addition, the interface corresponding to the "Me" control 503 further includes a "Security threshold" setting control 5032. The user may set a security threshold by using the "Security threshold" setting control 5032. If the mobile phone 100 detects a trigger operation performed by the user on the "Security threshold" setting control 5032, the mobile phone 100 displays a security threshold input box. The user can enter a security threshold in the security threshold input box, and then tap an "OK" control to save the entered security threshold.

The interface corresponding to the "Me" control 503 further includes a "Model training period" setting control 5033. The user may set a model training period by using the "Model training period" setting control 5033.

The interface corresponding to the "Me" control 503 further includes a "Detection period" setting control 5034. The user may set a detection period of the mobile phone 100 by using the "Detection period" setting control 5034.

The interface corresponding to the "Me" control 503 may further include other controls for respectively setting a quantity of data segments of the difference adjustment data, setting an amount of initial PPG data obtained by the mobile phone 100, setting notification information, and setting user information, which may be selected based on a requirement.

In this implementation, the blood glucose detection application 500 may be, for example, a HiResearch-based health detection application or another application. Certainly, the blood glucose detection application may be an independent application, or may be a part of function implementation in an application.

In the blood glucose detection method provided in this implementation, the user can conveniently and quickly implement non-invasive blood glucose detection by using the blood glucose detection application 500, to implement high blood glucose screening and blood glucose monitoring, so as to improve user experience.

The solution provided in this application is not only applicable to screening for high blood glucose, but also applicable to screening for low blood glucose. That is, in another implementation of this application, the foregoing PPG data of the group of people with high blood glucose may also be PPG data of a group of people with low blood glucose.

In this case, a process in which the mobile phone 100 generates the blood glucose detection model based on the blood glucose detection model training method provided in this application includes: The mobile phone 100 obtains initial PPG data from the server 300, where the initial PPG data includes PPG data of a group of healthy people and PPG data of a group of people with low blood glucose. The mobile phone 100 obtains, from each of the PPG data of the group of healthy people and the PPG data of the group of people with low blood glucose, PPG data used to represent different blood glucose levels and uses the PPG data as difference adjustment data, and performs feature extraction on the difference adjustment data to obtain difference adjustment feature data. The mobile phone 100 obtains difference adjustment values based on the difference adjustment feature data, and then performs, based on the difference adjustment values, difference amplification processing on the initial PPG data on which feature extraction is performed, to obtain model training PPG feature data. The mobile phone 100 performs model training based on the model training PPG feature data, to obtain a blood glucose detection model.

A detailed process in which the mobile phone 100 obtains the blood glucose detection model based on the initial PPG data including the PPG data of the group of healthy people and the PPG data of the group of people with low blood glucose is similar to the foregoing process in which the mobile phone 100 obtains the blood glucose detection model based on the initial PPG data including the PPG data of the group of healthy people and the PPG data of the group of people with high blood glucose. Details are not described herein again.

Blood glucose information in the PPG data can be amplified differently by using the difference adjustment data, so that a problem that the blood glucose information in the PPG data is weak is resolved. Therefore, according to the PPG-based blood glucose detection model training method provided in this application, the blood glucose detection result output by the obtained blood glucose detection model during blood glucose detection can be more accurate. That is, when low blood glucose screening is performed, a screening result can be more accurate.

In another implementation of this application, if the blood glucose detection model is a detection model obtained by the mobile phone 100 by performing model training based on initial PPG data including PPG data of a group of healthy people and PPG data of a group of people with low blood glucose, the blood glucose detection method provided in this application may be used to screen for hypoglycemia. To be specific, the mobile phone 100 inputs to-be-measured PPG data into the blood glucose detection model, to obtain a blood glucose detection result, and the obtained blood glucose detection result is more accurate.

In this implementation, the blood glucose detection result may be a low blood glucose screening result, and the blood glucose screening result may be a low blood glucose risk probability value. The blood glucose detection information may include low blood glucose risk level information and user reminder information. The low blood glucose risk level information may be a plurality of types of low blood glucose risk level information determined based on the low blood glucose risk probability value, for example, may be a high risk, a medium risk, and a low risk. The user reminder information may be information such as suggestion information used to remind the user to perform low blood glucose prevention.

In addition, in this implementation, interfaces of the mobile phone 100 and the mobile phone 600 may correspond to FIG. 6B to FIG. 6G, provided that "high blood glucose" in FIG. 6B to FIG. 6G is replaced with and displayed as "low blood glucose". Details are not described in this application again.

Certainly, in this implementation, a security threshold corresponding to "low blood glucose" may be the same as or different from a security threshold corresponding to "high blood glucose", and may be set based on a requirement.

In addition, in another implementation of this application, PPG data of a group of people with abnormal blood glucose may alternatively include both PPG data of a group of people with high blood glucose and PPG data with a group of people with low blood glucose.

That is, in another implementation of this application, the blood glucose detection model training method includes: When performing detection model training, the mobile phone 100 may set a group of people type identifier corresponding to the PPG data of the group of healthy people to 0, set a group of people type identifier corresponding to the PPG data of the group of people with high blood glucose to 1, and set a group of people type identifier corresponding to the PPG data of the group of people with low blood glucose to 2. The mobile phone 100 obtains, from each of the PPG data of the group of healthy people, the PPG data of the group of people with high blood glucose, and the PPG data of the group of people with low blood glucose, PPG data used to represent different blood glucose levels and uses the PPG data as difference adjustment data, and performs feature extraction on the difference adjustment data to obtain difference adjustment feature data. The mobile phone 100 obtains difference adjustment values based on the difference adjustment feature data, and then performs, based on the difference adjustment values, difference amplification processing on the initial PPG data on which feature extraction is performed, to obtain model training PPG feature data. The mobile phone 100 performs model training based on the model training PPG feature data, to obtain a blood glucose detection model.

A detailed process in which the mobile phone 100 obtains the blood glucose detection model based on the initial PPG data including the PPG data of the group of healthy people, the PPG data of the group of people with high blood glucose, and the PPG data of the group of people with low blood glucose is similar to the foregoing process in which the mobile phone 100 obtains the blood glucose detection model based on the initial PPG data including the PPG data of the group of healthy people and the PPG data of the group of people with high blood glucose. Details are not described herein again.

Blood glucose information in the PPG data can be amplified differently by using the difference adjustment data, so that a problem that the blood glucose information in the PPG data is weak is resolved. Therefore, according to the PPG-based blood glucose detection model training method provided in this implementation, the blood glucose detection result output by the obtained blood glucose detection model during blood glucose detection can be more accurate. That is, when abnormal blood glucose screening is performed, a screening result can be more accurate.

In another implementation of this application, the blood glucose detection method includes: The mobile phone 100 inputs to-be-measured PPG data into the blood glucose detection model, to obtain a blood glucose detection result; and performs blood glucose detection based on the blood glucose detection model, where the obtained blood glucose detection result includes a high blood glucose detection result and a low blood glucose detection result, and the obtained blood glucose detection result is more accurate.

Figure 6H:
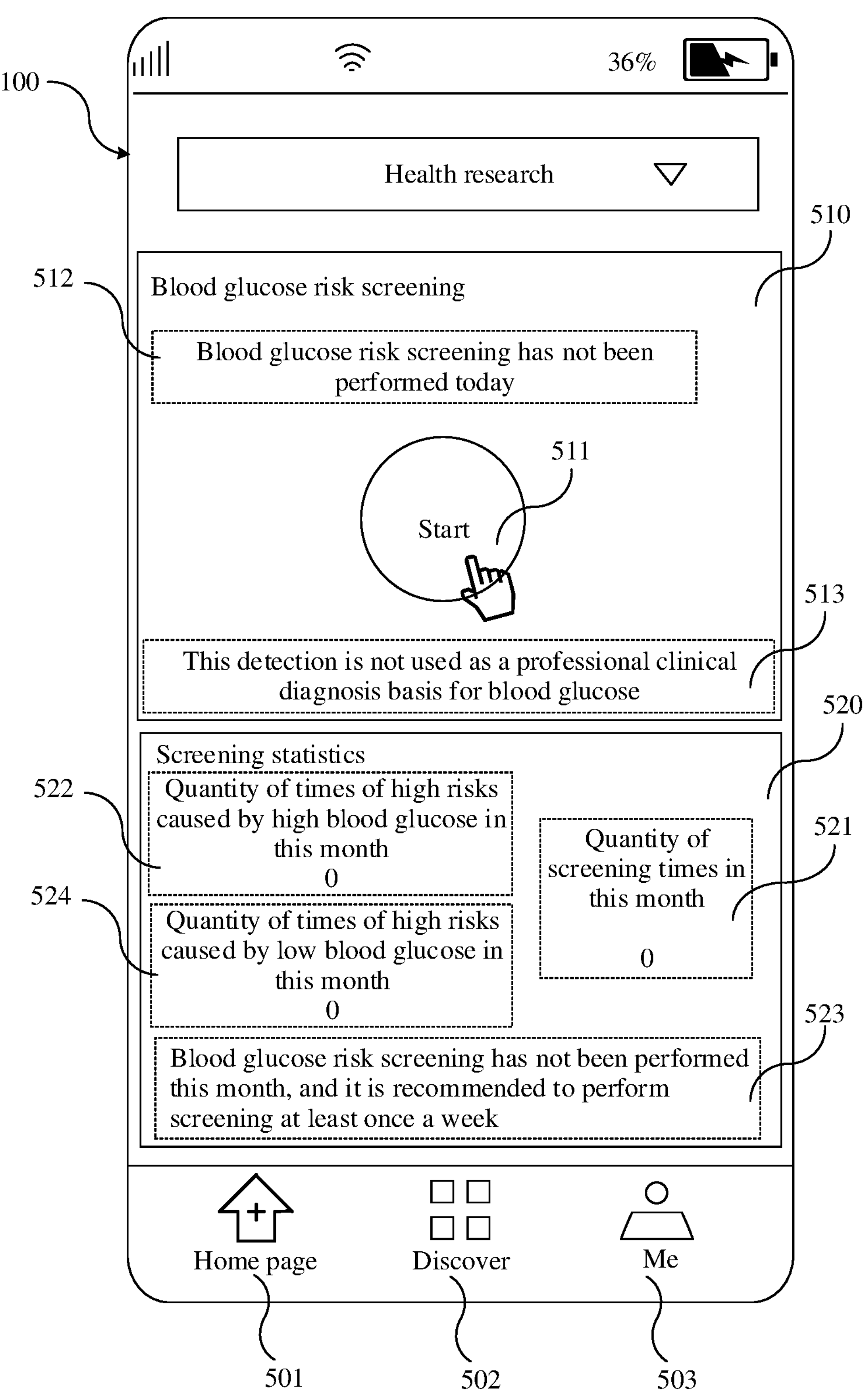

In addition, in this implementation, an interface of the mobile phone 100 corresponding to FIG. 6B may be shown in FIG. 6H. The first display area 510 of the mobile phone 100 is a status description area of "Blood glucose risk screening". The first user reminder information 512 may display "Blood glucose risk screening has not been performed today". The second user reminder information 513 may display "This detection is not used as a professional clinical diagnosis basis for blood glucose".

The third user reminder information 523 in the second display area 520 may display "Blood glucose risk screening has not been performed this month, and it is recommended to perform screening at least once a week".

In addition, the quantity 522 of high-risk times in this month in the second display area 520 may be a quantity 522 of times of high risks caused by high blood glucose in this month. The second display area 520 may further include a quantity 524 of times of high risks caused by low blood glucose in this month.

In addition, for interfaces of the mobile phone 100 and the mobile phone 600 corresponding to FIG. 6C to FIG. 6G, controls corresponding to a "high blood glucose detection result" and a "low blood glucose detection result" may be separately set based on a requirement. Details are not described in this application.

Figure 7:
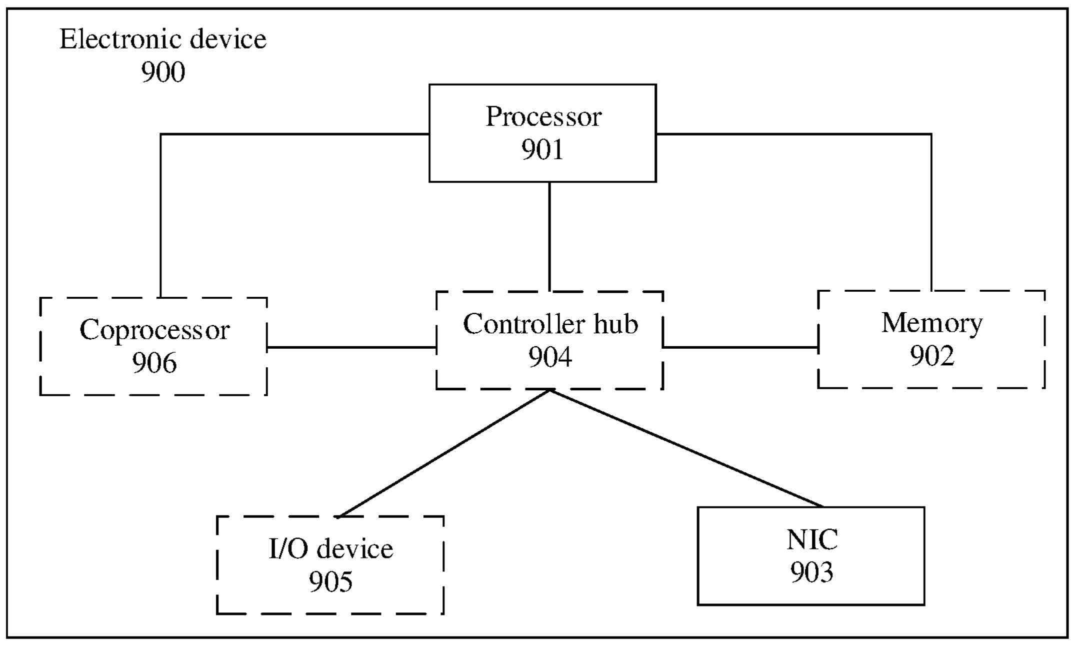
FIG. 7 is a schematic diagram of a structure of an electronic device according to some embodiments of this application.

FIG. 7 is a schematic diagram of a structure of an electronic device 900 according to an implementation of this application. The electronic device 900 may include one or more processors 901 coupled to a controller hub 904. In at least one embodiment, the controller hub 904 communicates with the processor 901 through a multi-branch bus such as a front side bus (FSB), a point-to-point interface such as a quick path interconnect (QPI), or a similar connection. The processor 901 executes instructions for controlling a general type of data processing operation. In an embodiment, the controller hub 904 includes but is not limited to a graphics memory controller hub (GMCH) (not shown in the figure) and an input/output hub (IOH) (which may be on separate chips) (not shown in the figure). The GMCH includes a memory and a graphics controller, and is coupled to the IOH.

The electronic device 900 may further include a coprocessor 906 and a memory 902 that are coupled to the controller hub 904. Alternatively, one or both of the memory 902 and the GMCH may be integrated into the processor 901 (as described in this application). The memory 902 and the coprocessor 906 are directly coupled to the processor 901 and the controller hub 904. The controller hub 904 and the IOH are located in a single chip.

The memory 902 may be, for example, a dynamic random access memory (DRAM), a phase change memory (PCM), or a combination thereof.

In an embodiment, the coprocessor 906 is a dedicated processor, for example, a high throughput MIC processor, a network or communications processor, a compression engine, a graphics processor, a GPGPU, or an embedded processor. An optional property of the coprocessor 906 is shown in FIG. 7 in dashed lines.

In an embodiment, the electronic device 900 may further include a network interface (NIC) 903. The network interface 903 may include a transceiver, configured to provide a radio interface for the electronic device 900 to further communicate with any other suitable devices (such as a front-end module and an antenna). In various embodiments, the network interface 903 may be integrated with another component of the electronic device 900. The network interface 903 may implement a function of a communications unit in the foregoing embodiment.

The electronic device 900 may further include an input/output (I/O) device 905. The input/output (I/O) device 905 may include a user interface through which a user can interact with the electronic device 900; a peripheral component interface through which a peripheral component can also interact with the electronic device 900; and/or a sensor, configured to determine an environmental condition and/or location information associated with electronic device 900.

It should be noted that FIG. 7 is merely used as an example. To be specific, although FIG. 7 shows that the electronic device 900 includes a plurality of components such as the processor 901, the controller hub 904, and the memory 902, in actual application, a device using the methods in this application may include only some of the components of the electronic device 900, for example, may include only the processor 901 and the NIC 903. A property of an optional component in FIG. 7 is shown by a dashed line.

The memory of the electronic device 900 may include one or more tangible and non-transitory computer-readable storage media configured to store data and/or instructions. The computer-readable storage medium stores instructions, and specifically, stores temporary and permanent copies of the instructions.

In this application, the electronic device 900 may be specifically a terminal device such as a mobile phone, a tablet computer, a personal digital assistant (Personal Digital Assistant, PDA), or a desktop computer. The instructions stored in the memory of the electronic device may include instructions that enable the electronic device to implement the blood glucose detection model training method and the blood glucose detection method mentioned above when being executed by at least one unit of the processor.

Figure 8:
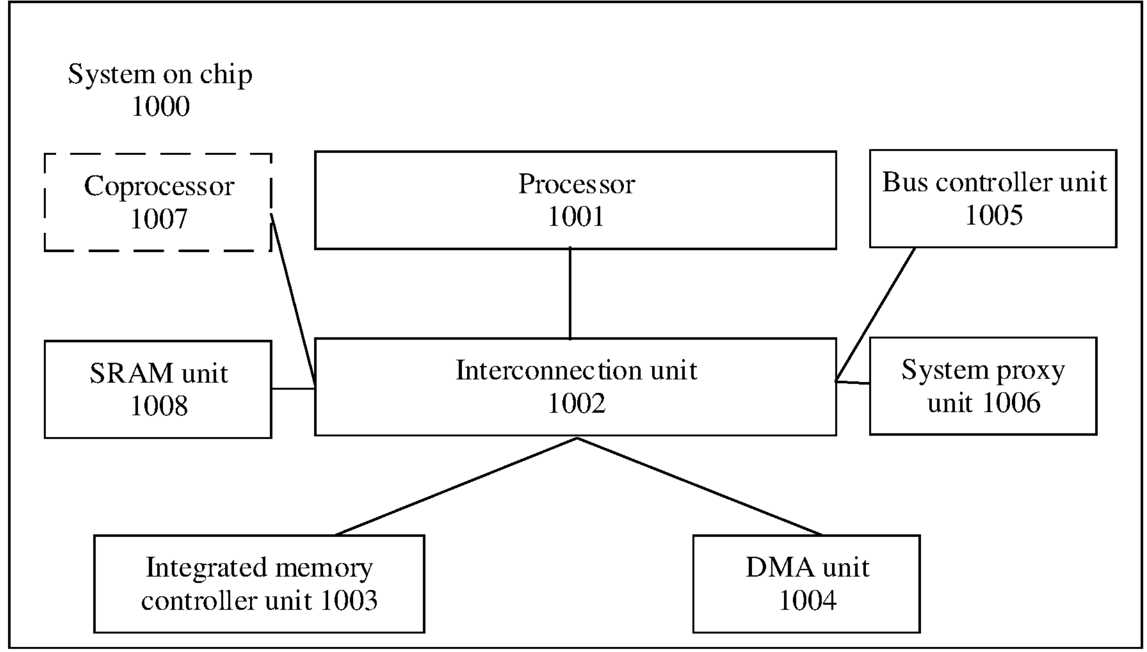
FIG. 8 is a schematic diagram of a structure of a system on chip (SoC) according to some embodiments of this application.

FIG. 8 is a schematic diagram of a structure of an SoC (System on Chip, system on chip) 1000 according to an implementation of this application. In FIG. 8, similar components are represented by a same reference numeral. In addition, a dashed-line box represents an optional feature of a more advanced SoC 1000. The SoC 1000 may be used in any electronic device according to this application, and may implement corresponding functions based on different devices in which the SoC 1000 is located and different instructions stored in the SoC 1000.

In FIG. 8, the SoC 1000 includes an interconnection unit 1002 coupled to a processor 1001, a system agent unit 1006, a bus controller unit 1005, an integrated memory controller unit 1003, a group of or one or more coprocessors 1007 that may include integrated graphics logic, an image processor, an audio processor, and a video processor, an SRAM (static random access memory) unit 1008, and a DMA (direct memory access) unit 1004. In an embodiment, the coprocessor 1007 includes a dedicated processor, for example, a network or communications processor, a compression engine, a GPGPU, a high throughput MIC processor, or an embedded processor.

The SRAM unit 1008 may include one or more computer-readable media configured to store data and/or instructions. The computer-readable storage medium may store instructions, and specifically, store temporary and permanent copies of the instructions. The instructions may include instructions that enable the electronic device to implement the blood glucose detection method mentioned above when being executed by at least one unit of the processor.

Embodiments of the mechanism disclosed in this application may be implemented in a manner such as software, hardware, firmware, or a combination of these implementation methods. Embodiments of this application may be implemented as a computer program or program code executed on a programmable system. The programmable program includes at least one processor and a memory (or a storage system, including volatile and nonvolatile memories and/or a storage unit).

It should be noted that the terms “first”, “second”, and the like are merely used for distinction and description, but cannot be understood as indicating or implying relative importance.

It should be noted that, in the accompanying drawings, some structural or method features may be shown in a particular arrangement and/or order. However, it should be understood that such a particular arrangement and/or order may not be required. In some implementations, these features may be arranged in a manner and/or order different from that shown in the descriptive accompanying drawings. In addition, inclusion of the structural or method features in a particular figure does not imply that such features are required in all implementations, and in some implementations, these features may not be included or may be combined with other features.

Although this application has been illustrated and described with reference to some example implementations of this application, a person of ordinary skill in the art should understand that the foregoing content is further detailed descriptions of this application with reference to specific implementations, and it cannot be considered that specific implementations of this application are merely limited to these descriptions. A person skilled in the art may make various changes in form and details, including making several simple deductions or replacements, without departing from the spirit and scope of this application.

What is claimed is:

1. A method for blood glucose detection, the method comprising:

obtaining, by a first electronic device, to-be-measured PPG (Photoplethysmography) data when the first electronic device detects a blood glucose detection instruction of a first user;

performing feature extraction on the to-be-measured PPG data in order to obtain to-be-measured PPG feature data;

inputting the to-be-measured PPG feature data into a pre-trained blood glucose detection model and obtaining a blood glucose detection result; and displaying first information according to the blood glucose detection result, wherein the blood glucose detection model is generated by performing machine learning training based on machine learning training PPG feature data, the machine learning training PPG feature data obtained by:

obtaining initial PPG data comprised of PPG data of a group of healthy people and PPG data of a group of people with abnormal blood glucose;

obtaining, from each of the PPG data of the group of healthy people and the PPG data of the group of people with abnormal blood glucose, PPG data used to represent different blood glucose levels and using the PPG data as difference adjustment data, and obtaining difference adjustment values based on the difference adjustment data; and performing, based on difference adjustment values, difference amplification processing on the initial PPG data on which feature extraction is performed in order to obtain the machine learning training PPG feature data.

2. The method according to claim 1, further comprising sending second information to a second electronic device when a historical blood glucose detection result satisfies a first condition, wherein the second electronic device corresponds to a user related to the first user.

3. The method according to claim 1, wherein obtaining the to-be-measured PPG data comprises both:

obtaining the to-be-measured PPG data based on a preset detection period; and opening a blood glucose detection application thereby displaying an application interface, wherein a blood glucose detection control is displayed in the application interface and obtaining the to-be-measured PPG data when detecting a trigger operation performed by a user on the blood glucose detection control.

4. The method according to claim 3, wherein the blood glucose detection result comprises a blood glucose abnormality risk probability value, and wherein the method further comprises:

obtaining a blood glucose abnormality risk level based on the blood glucose abnormality risk probability value, collecting statistics about a quantity of times that a risk level is a high risk within a preset time period, and when a quantity of high-risk times exceeds a security threshold, generating first notification information and sending the first notification information to an associated device corresponding to an associated person, or when a quantity of high-risk times is less than a security threshold, generating second notification information and sending the second notification information to an associated device corresponding to an associated person.

5. The method according to claim 4, wherein the blood glucose detection application further comprises an associated person setting control, and wherein the method further comprises:

receiving a trigger operation performed by the user on the associated person setting control, and performing an associated person addition, modification, or deletion operation based on the trigger operation of the user.

6. The method according to claim 4, wherein the blood glucose detection application further comprises a security threshold setting control, and wherein the method further comprises receiving a security threshold setting performed by the user by using the security threshold setting control.

7. The method according to claim 3, further comprising:

displaying blood glucose detection information in the application interface, wherein the blood glucose detection information comprises blood glucose abnormality risk screening result information and user reminder information that are generated based on the blood glucose detection result, wherein the blood glucose abnormality risk screening result information comprises a blood glucose abnormality risk level, and wherein the user reminder information comprises a quantity of blood glucose detection times, a quantity of times that a quantity of high-risk times exceeds a security threshold, and suggestion information used for health intervention.

8. The method according to claim 3, further comprising obtaining the to-be-measured PPG data from a wearable device that establishes a communication connection to the first electronic device and that is used to detect PPG data.

9. A first electronic device comprising:

at least one memory; and at least one processor configured to execute a computer program stored in the at least one memory, the computer program including instructions for:

obtaining to-be-measured PPG (Photoplethysmography) data when the first electronic device detects a blood glucose detection instruction of a first user;

performing feature extraction on the to-be-measured PPG data in order to obtain to-be-measured PPG feature data;

inputting the to-be-measured PPG feature data into a pre-trained blood glucose detection model and obtaining a blood glucose detection result; and displaying first information according to the blood glucose detection result, wherein the blood glucose detection model is generated by performing machine learning training based on machine learning training PPG feature data, the machine learning training PPG feature data obtained by:

obtaining initial PPG data comprised of PPG data of a group of healthy people and PPG data of a group of people with abnormal blood glucose;

obtaining, from each of the PPG data of the group of healthy people and the PPG data of the group of people with abnormal blood glucose, PPG data used to represent different blood glucose levels and using the PPG data as difference adjustment data, and obtaining difference adjustment values based on the difference adjustment data; and performing, based on difference adjustment values, difference amplification processing on the initial PPG data on which feature extraction is performed, in order to obtain the machine learning training PPG feature data.

10. The first electronic device according to claim 9, further comprising instructions for sending second information to a second electronic device when a historical blood glucose detection result satisfies a first condition, wherein the second electronic device corresponds to a user related to the first user.

11. The first electronic device according to claim 9, further comprising instructions for both:

obtaining the to-be-measured PPG data based on a preset detection period; and opening a blood glucose detection application thereby displaying an application interface, wherein a blood glucose detection control is displayed in the application interface and obtaining the to-be-measured PPG data when detecting a trigger operation performed by a user on the blood glucose detection control.

12. The first electronic device according to claim 11, wherein the blood glucose detection result comprises a blood glucose abnormality risk probability value, and wherein the first electronic device further comprises instructions for:

obtaining a blood glucose abnormality risk level based on the blood glucose abnormality risk probability value, collecting statistics about a quantity of times that a risk level is a high risk within a preset time period, and when a quantity of high-risk times exceeds a security threshold, generating first notification information and sending the first notification information to an associated device corresponding to an associated person, or when a quantity of high-risk times is less than a security threshold, generating second notification information, and sending the second notification information to an associated device corresponding to an associated person.

13. The first electronic device according to claim 12, wherein the blood glucose detection application further comprises an associated person setting control, and wherein the first electronic device further comprises instructions for:

receiving a trigger operation performed by the user on the associated person setting control, and performing an associated person addition, modification, or deletion operation based on the trigger operation of the user.

14. The first electronic device according to claim 12, wherein the blood glucose detection application further comprises a security threshold setting control, and wherein the first electronic device further comprises instructions for receiving a security threshold setting performed by the user by using the security threshold setting control.

15. The first electronic device according to claim 9, further comprising instructions for:

displaying blood glucose detection information in an application interface, wherein the blood glucose detection information comprises blood glucose abnormality risk screening result information and user reminder information that are generated based on the blood glucose detection result, wherein the blood glucose abnormality risk screening result information comprises a blood glucose abnormality risk level, and wherein the user reminder information comprises a quantity of blood glucose detection times, a quantity of times that a quantity of high-risk times exceeds a security threshold, and suggestion information used for health intervention.

16. The first electronic device according to claim 9, further comprising instructions for obtaining the to-be-measured PPG data from a wearable device that establishes a communication connection to the first electronic device and that is used to detect PPG data.

17. A blood glucose detection machine learning training method comprising:

obtaining, by a first electronic device, initial PPG (Photoplethysmography) data, wherein the initial PPG data comprises PPG data of a group of healthy people and PPG data of a group of people with abnormal blood glucose;

obtaining, from each of the PPG data of the group of healthy people and the PPG data of the group of people with abnormal blood glucose, PPG data used to represent different blood glucose levels and using the PPG data as difference adjustment data, and obtaining difference adjustment values based on the difference adjustment data;

performing, based on the difference adjustment values, difference amplification processing on the initial PPG data on which feature extraction is performed in order to obtain machine learning training PPG feature data; and performing machine learning training based on the machine learning training PPG feature data in order to obtain a blood glucose detection model.

18. The blood glucose detection machine learning training method according to claim 17, wherein performing, based on the difference adjustment values, the difference amplification processing on the initial PPG data on which the feature extraction is performed in order to obtain machine learning training PPG feature data comprises:

obtaining differences between the initial PPG data on which the feature extraction is performed and the difference adjustment values, and obtaining the machine learning training PPG feature data based on the differences; or obtaining sums of the initial PPG data on which the feature extraction is performed and the difference adjustment values, and obtaining the machine learning training PPG feature data based on the sums.

* * * * *